United States Patent [19]
Feng et al.

[11] Patent Number: 5,972,670
[45] Date of Patent: Oct. 26, 1999

[54] BLUE COPPER OXIDASE MUTANTS WITH ENHANCED ACTIVITY

[76] Inventors: Xu Feng, 1534 Carmel Valley Dr., Woodland, Calif. 95776; Randy M. Berka, 3609 Modoc Pl.; Jill Angela Wahleithner, 1718 Tea Pl., both of Davis, Calif. 95616

[21] Appl. No.: 09/005,397

[22] Filed: Jan. 9, 1998

Related U.S. Application Data

[62] Division of application No. 08/706,037, Aug. 30, 1996, Pat. No. 5,770,419.

[51] Int. Cl.⁶ ...................................................... C12N 9/02

[52] U.S. Cl. .................. 435/189; 435/252.33; 435/254.2; 435/254.3; 435/320.1; 536/23.2

[58] Field of Search ............................. 435/189, 252–33, 435/254.2, 254.3, 320.1, 254.1; 536/23.2

[56] References Cited

U.S. PATENT DOCUMENTS 5,480,801   1/1996   Wahleithner et al. ............... 435/254.3

FOREIGN PATENT DOCUMENTS

| 0 506 431 A1 | 3/1992 | European Pat. Off. . |
| WO 92/01046 | 1/1992 | WIPO . |
| WO 95/07988 | 3/1995 | WIPO . |
| WO 95/33836 | 12/1995 | WIPO . |

OTHER PUBLICATIONS

Germann, Ursula A. et al., "Characterization of Two Allelic Forms of Neurospora Crassa Laccase", 1988 by The American Society For Biochemistry And Molecular Biology, Inc., Jan. 15, vol. 263, No. 2, pp. 885–896.

Kojima Yasushi et al., "Cloning, Sequence Analysis, and Expression of Ligninolytic Phenoloxidase Genes of the White–rot Basidiomycete Coriolus", 1990 by The American Society of Biochemistry And Molecular Biology, vol. 265, No. 25, Sep. 5, pp. 15224–15230.

Askwith, Candice et al., "The FET3 Gene of *S. Cerevisiae* Encodes A Multicopper Oxidase Required For Ferrous Iron Uptake", Jan. 28, 1994, by Cell Press, vol. 76, pp. 403–410.

*Primary Examiner*—Ponnathapura Achutamurthy
*Assistant Examiner*—Nashaat T. Nashed
*Attorney, Agent, or Firm*—Steve T. Zelson; Elias J. Lambiris; Robert L. Starnes

[57] ABSTRACT

The present invention relates to mutants of a blue multi-copper oxidase, comprising (a) a substitution of one or more amino acid residues with other amino acid residues, (b) an insertion of one or more amino acid residues and/or (c) a deletion of one or more amino acid residues, wherein the substitution, insertion or deletion is carried out at a position which is located no greater than 15 Å from a Type I (T1) copper site. The present invention also relates to nucleic acid constructs comprising a nucleic acid sequence encoding the mutants of the present invention, host cells comprising the construct of the present invention, and methods for producing mutants of the present invention.

20 Claims, 20 Drawing Sheets

```
        87              96          105         114         123         132
ATG CTT TCT AGC ATT ACC CTC CTA CCT TTG CTC GCT CCT TCA ACC CCC GCC
 M   L   S   S   I   T   L   L   P   L   L   A   P   S   T   P   A 141             150         159         168         177         186
TTT GCT GCC GTC CGC AAC TAT AAG TTC GAC ATC GCT AAG AAC GTC GCT CCC
 F   A   A   V   R   N   Y   K   F   D   I   A   K   N   V   A   P 195             204         213         222         231         240
GAT GGC TTT CAG CGC TCT ATC GTC TCC ATC GTC AAC GGT TTA GTT CCT GGC ACG TTG
 D   G   F   Q   R   S   I   V   S   I   V   N   G   L   V   P   G   T   L 249             258         267         276         285         294
ATC ACG GCC AAC AAG GGT GAC ACC TTG CGC ATT AAT GTC ACG CAA CTC AAT CAA ACG
 I   T   A   N   K   G   D   T   L   R   I   N   V   T   Q   L   N   Q   T 303             312         321         330         339         348
GAC CCT AGT ATG CGT GCC ACA ACG ATT CAT TGG CAT GTC ACG TTG GGA TTC CAA GCT
 D   P   S   M   R   A   T   T   I   H   W   H   V   T   L   G   F   Q   A 357             366         375         384         393         402
ACT ACC GCC GAC GAG GAT GGC CCC GCA TTC GTC ACG CAA TGC CCT ATT GCG CAA
 T   T   A   D   E   D   G   P   A   F   V   T   Q   C   P   I   A   Q
```

```
              411            420            429            438            447            456
AAT  TTG  TCC  TAT  ACA  GAG  ATC  CCA  TTG  CGC  GGC  CAA  ACA  GGA  ACC  ATG  TGG
 N    L    S    Y    T    E    I    P    L    R    G    Q    T    G    T    M    W 465            474            483            492            501            510
TAT  CAC  GCC  CAT  CTT  GCG  AGT  CAA  TAT  GTC  GAT  GGA  TTG  CGA  GGC  CCT  TTG  GTC
 Y    H    A    H    L    A    S    Q    Y    V    D    G    L    R    G    P    L    V 519            528            537            546            555            564
ATC  TAT  GAT  CCA  AAC  CTT  ATG  CCA  AAG  TCG  CGC  TAC  GAC  GTG  GGC  GAT  GCG  AGC
 I    Y    D    P    N    L    M    P    K    S    R    Y    D    V    G    D    A    S 573            582            591            600            609            618
ACA  GTC  ATG  GAG  GAC  TGG  TAC  CAT  ACT  CCG  GCA  CCC  GTT  CCG  GAT  GCG  GAA  AAG
 T    V    M    E    D    W    Y    H    T    P    A    P    V    P    D    A    E    K 627            636            645            654            663            672
CAA  TTC  TCG  ACT  AAT  AAC  ACC  GCT  CTG  CTC  TCT  CCT  GTT  CCG  GAC  TCG  GGT
 Q    F    S    T    N    N    T    A    L    L    S    P    V    P    D    S    G 681            690            699            708            717            726
CTT  ATC  AAT  GGC  AAA  GGG  CGC  TAT  GTG  GGC  GGT  CCC  GCA  GTT  CCC  CGG  TCA  GTA
 L    I    N    G    K    G    R    Y    V    G    G    P    A    V    P    R    S    V
```

```
            735         744         753         762         771         780
ATC AAC GTA AAA CGT GGG AAA CGA TAT CGC TTG GTA ATC AAC GCT TCT GCT
 I   N   V   K   R   G   K   R   Y   R   L   V   I   N   A   S   A 789         798         807         816         825         834
ATC GGG TCG TTT ACC TTT TCG ATC GAA GGA CAT AGT CTG ACT GTC ATT GAG GCC
 I   G   S   F   T   F   S   I   E   G   H   S   L   T   V   I   E   A 843         852         861         870         879         888
GAT GGG ATC CTG CAC CAG CCC TTG GCT GTT GAC AGC TTC CAG ATT TAC GCT GGA
 D   G   I   L   H   Q   P   L   A   V   D   S   F   Q   I   Y   A   G 897         906         915         924         933         942
CAA CGC TAC TCT GTC ATC GTT GAA GCC AAC CAA ACC GCC GCC AAC ATT TGG ATT
 Q   R   Y   S   V   I   V   E   A   N   Q   T   A   A   N   I   W   I 951         960         969         978         987         996
CGT GCA CCA ATG ACC GTT GCA GGA GCC GGA ACC AAT GCA AAC TTG GAC CCC ACC
 R   A   P   M   T   V   A   G   A   G   T   N   A   N   L   D   P   T 1005        1014        1023        1032        1041        1050
AAT GTC TTT GCC GTA TTG CAC TAC GAG GGA GCG CCC AAC GAA CCC ACG ACG
 N   V   F   A   V   L   H   Y   E   G   A   P   N   E   P   T   T
```

Fig. 6C

```
     1059            1068            1077            1086            1095          1104
GAA CAA GGC AGT GCT ATC GGT ACT GCA CTC GTT GAG AAC CTC CAT GCG CTC
 E   Q   G   S   A   I   G   T   A   L   V   E   N   L   H   A   L 1113            1122            1131            1140            1149          1158
ATC AAC CCT GGC GCT CCG GGC TCC GGC GCT CCC GCA GAC GTT TCC CTC AAT CTT
 I   N   P   G   A   P   G   S   G   A   P   A   D   V   S   L   N   L 1167            1176            1185            1194            1203          1212
GCA ATT GGG CGC AGC ACA GTT GAT GGG ATT CTT AGG TTC ACA TTT AAT AAC ATC
 A   I   G   R   S   T   V   D   G   I   L   R   F   T   F   N   N   I 1221            1230            1239            1248            1257          1266
AAG TAC GAG GCT CCT TCG TTG CCC ACG CTC TTG AAG ATT TTG GCA AAC AAT GCG
 K   Y   E   A   P   S   L   P   T   L   L   K   I   L   A   N   N   A 1275            1284            1293            1302            1311          1320
AGC AAT GAC GCC GAT TTC ACG CCA AAT GAG CAC ACT ATC GTA TTG CCA CAC AAT
 S   N   D   A   D   F   T   P   N   E   H   T   I   V   L   P   H   N 1329            1338            1347            1356            1365          1374
AAA GTT ATC GAG CTC AAT ATC ACC GGA GGT GCA GAC CAC CCT ATC CAT CTC CAC
 K   V   I   E   L   N   I   T   G   G   A   D   H   P   I   H   L   H
```

Fig. 6D

```
     1383           1392           1401           1410           1419           1428
GGC  CAT  GTG  TTT  GAT  ATC  GTC  AAA  TCA  CTC  GGT  GGT  ACC  CCG  AAC  TAT  GTC  AAC
 G    H    V    F    D    I    V    K    S    L    G    G    T    P    N    Y    V    N 1437           1446           1455           1464           1473           1482
CCG  CCA  CGC  AGG  GAC  GTA  GTT  CGT  GTC  GGA  GGC  ACC  GGT  GTG  CTC  CGA  TTC
 P    P    R    R    D    V    V    R    V    G    G    T    G    V    L    R    F 1491           1500           1509           1518           1527           1536
AAG  ACC  GAT  AAC  CCA  GGC  CCA  TGG  TTT  GTT  CAC  TGC  CAC  ATT  GAC  TGG  CAC  TTG
 K    T    D    N    P    G    P    W    F    V    H    C    H    I    D    W    H    L 1545           1554           1563           1572           1581           1590
GCT  GGG  CTC  GCA  CTT  TTT  GCC  GAG  GCC  CCC  AGC  CAG  ATT  CGC  CAG  GGT
 A    G    L    A    L    F    A    E    A    P    S    Q    I    R    Q    G 1599           1608           1617           1626           1635           1644
GAG  GCT  TCG  CAG  GTC  CAG  CTT  CCC  AAC  AAT  GCC  TGG  AAC  CAG  CTC  TGC  CCC  AAG  TAC  GCG
 E    A    S    Q    V    Q    L    P    N    N    A    W    N    Q    L    C    P    K    Y    A 1653           1662
GCT  CTT  CCT  CCC  GAT  TTG  CAG  T
 A    L    P    P    D    L    Q    *
```

Fig. 6E

```
gctagcttcttggtcaccgtcgtttcgcccgccccctcctccttcaaccccctgagtagtcggctaagcgatcctca    80
atctggtcttgtgaggtcacgtcctccagcagatgacagttcatcgagcgagtgatctccaccaccagaaggagggg   160
gatgcgcgcatgctccaacatccctggtgtcgctagagacgtcgcggcatcagcctttcatcacaccgagcacgtccac  240
ggaccggctcctttcaccccgcgtcctccggaggattgagtcacgatatttcggatgtgggaaggggagagaaagga   320
ggggggaggggcggaaacatgttggatacgagctgcgcccctttttcaacatcgagaacaggaagtcgttggtgtcggcc   400
gtaatgtctataaacgaggctcctctcgtcgtcgacttgtctcaggttctctctcgtccacaccaagccagtcttg    480
cctgagccacctgagccacttcaactcatcatcttcagtcaagtcgttcattgacattgtgtctctttctatcgagt   560
cggcttcccgcccttcaccacaacATGAAGTCCTTCATCAGCGCCGCCGACGCTTTTGGTGGGCATTCTCACCCCTAGCG   640
                        MetLysSerPheIleSerAlaAlaThrLeuLeuValGlyIleLeuThrProSerV    -29
TTGCTGCTGCCCCTCCATCCACCCTGAGCAGCGGCGACCTGCTCGTCCGATCACGGAGAGGAGGCAGCCGTGAAG       720
alAlaAlaAlaProSerThrProGluGlnArgAspLeuLeuValProIleThrGluArgGluAlaAlaValLys        -3
GCTCGCCAGCAGAGCTGCAACACCCCAGCAACCGGGCGTGCTGACTGACGGATACGACATCAACACCGACTACGAAGT    800
AlaArgGlnSerCysAsnThrProSerAsnArgAlaCysTrpThrAspGlyTyrAspIleAsnThrAspTyrGluVa     25
```

Fig. 7A

```
GGACAGCCCGGACACGGGTGTGTTCGGCCGgtgagtgctctcgttaattacgcttcggcgagttgcgcagatatattaa    880
lAspSerProAspThrGlyValValArgPro                                                     35 atactgcaaacctaagcaggagctgacatgcgacagTACACTCTGACTCTCACCGAAGTCGACAACTGGACCGGACCTGA    960
                                    TyrThrLeuThrLeuThrGluValAspAsnTrpThrGlyProAs   50

TGGCGTCGTCAAGGAGAAGGTCATGCTGGTTAACAgtacggcaccccttttcttgtcctaggatctgggtgatgtgcgtc   1040
pGlyValValLysGluLysValMetLeuValAsnA                                                 62 gttgcccctgagagagactgaccgagcctttggctgtgcagATAGTATAATCGgtaattaattatacgccctgcctccagc  1120
                                         snSerIleIleG                              66 agccccagcagctcgagaaagggtatctgaagttagtcaggcctgacctgaccggggccaacccaccatagGACCAAC     1200
                                                                      lyProTh      68

AATCTTTGCGGGACTGGGGCGACACGGATCCAGGTAACGGTCATCAACAACCTCGAGACCAACGGgtatgtctgctgttgc 1280
rIlePheAlaAspTrpGlyAspThrAspProGlyAsnGlyHisGlnGlnProArgAspGlnArg                    89

( approximate: rIlePheAlaAspTrpGlyAspThrAspProGlyAsnGlyHisGlnGlnProArgAspGlnArg )

tctcttgctctccctcgtccgcgactaataatatcaactcgtgtggaaaacagCACGTCGATCCACTGGCACGGACTG     1360
                                                     yThrSerIleHisTrpHisGlyLeu      97
```

Fig. 7B

```
CACCAGAAGGGCACCAACCTGCAGCACGACGGGCGCCAACGGTATCACCGAGTGCCCGATCCCGCCCAAGGGAGGGAGGAAGGT    1440
HisGlnLysGlyThrAsnLeuHisAspLeuHisAspGlyAlaAsnGlyIleThrGluCysProIleProProLysGlyGlyArgLysVa    124

GTACCGGTTCAAGGCTCAGCAGTACGGGACGAGCTGGTTACCACTCGCACTTCTCGGCCCAGTACGGCAACGGCGTGGTCG       1520
lTyrArgPheLysAlaGlnGlnTyrGlyThrSerTrpTyrHisSerHisPheSerAlaGlnTyrGlyAsnGlyValValG           151

GGGCCATTCAGATCAACGGGCCTCGCTGCCGTACGACACCGACCTGGGCGTGTTCCCCATCAGCGACTACTACTAC            1600
lyAlaIleGlnIleAsnGlyProAlaSerLeuProTyrAspThrAspLeuGlyValPheProIleSerAspTyrTyrTyr          177

AGCTCGGCCGACGAGCTGGTGGAACTCACCAAGAACTCACCAAGAACTCCTTCAGCGACAACGTCCTGTTCAACGGCACGGC      1680
SerSerAlaAspGluLeuValGluLeuThrLysAsnSerGlyAlaProPheSerAspAsnValLeuPheAsnGlyThrAl           204

CAAGCACCCCGAGACGGGCGAGGGCGAGTACGCCAACGTGACGCTCACCCCGGAGCACCGCCTGCCGCTGCGCCTGATCA       1760
aLysHisProGluThrGlyGluGlyGluTyrAlaAsnValThrLeuThrProGlyArgArgHisArgProArgLeuArgLeuIleA     231

ACACGTCGGTCGAGAACCACTTCCAGGTCTCGCTCGTCAACCACCACACCATGACCATCATCGCCGCCGACATGGTGCCCGTC    1840
snThrSerValGluAsnHisPheGlnValSerLeuValAsnHisThrMetThrIleIleAlaAlaAspMetValProVal          257

AACGCCATGACGGTCGACAGCCTCTTCCTCGGCGTCGGCCAGCGCTACGATGTCGTCATCGAAGCCAGCCGAACGCCCGG       1920
AsnAlaMetThrValAspSerLeuPheLeuGlyValGlyGlnArgTyrAspValValIleGluAlaSerArgThrProGl          284
```

Fig. 7C

```
GAACTACTGGTTTAACGTCACATTTGGGCGGCCTGCTCTGCGGCGGCCTCCAGGAATCCCTACCCGGCCGCCATCTTCC    2000
yAsnTyrTrpPheAsnValThrPheGlyGlyLeuLeuCysGlyGlySerArgAsnProTyrProAlaAlaIlePheH       311

ACTACGCCGGGCCCCCGGGGCGGCCCCGCGGACGAGGGCAAGGCCCCGGTCGACCACAACTGCCTGGACCTCCCCAAC    2080
isTyrAlaGlyProGlyProProThrAspGluGlyLysAlaProValAspHisAsnCysLeuAspLeuProAsn          337

CTCAAGCCCGTCGTGGCCCGCGACGTGCCCTGAGCGGCTTCGCCAAGCGGCCCGACAACACGCTCGACGTCACCCTGA    2160
LeuLysProValValAlaArgaspValProLeuSerGlyPheAlaLysArgProAspAsnThrLeuAspValThrLeuAs    364

CACCACGGGCACGCCCCTGTTCGTCTGGAAGGTCAACGGCCATCAACATGACTGGGGCCAGGCCCGTCGTCGACT       2240
pThrThrGlyThrProLeuPheValTrpLysValAsnGlySerAlaIleAsnIleAspTrpGlyArgProValValAspT    391

ACGTCCTCACGCAGAACACCAGCTTCCACCCGGGTACAACATTGTCGAGGTGAACGGAGCTGATCAGgtaagaaaaagg    2320
yrValLeuThrGlnAsnThrSerPheProProGlyTyrAsnIleValGlyValAlaAsnGlyAlaAspGln             413 ggaccgcaggggtgctgctgcaagtacacccttgctcgcccctcctgttcctcctaataactacctcccaaccctccccc    2400 taattaattcacttaaaggccgatcaagactgaccgagccccctctcttgcagTGGTCGTACTGGTTGATCGAGAACG    2480
                                                     TrpSerTyrTrpLeuIleGlnAsnA    422
```

Fig. 7D

```
ATCCCGGGGCACCTTTCACCCTACCGCATCCGATGCACCTGCACgtaagttggatacatatatatatatacatt    2560
spProGlyAlaProPheThrLeuProHisProMetHisLeuHis                                   436 gctttcctggctcgctcccttaaataaattaaataacaaaaataacaaaaaaaagGGCCACGACTTTTACGTGCTGGG  2640
                                                       GlyHisAspPheTyrValLeuGl  444

CCGCTCGCCCGACGAGTCGCCGGCATCCAACGAGCGGCACGTGTTCGATCCGGCGCGGGCCTGCTGAGCGGGG      2720
yArgSerProAspGluSerAsnGluArgHisValPheAspProAlaArgAspAlaGlyLeuLeuSerGlyA         471

CCAACCCTGTGCGGGACGTGACGATGCTGCCGGCGTTCGGGTGGTGCCTTCCGGCCGACAACCCGGGC           2800
laAsnProValArgArgAspValSerMetLeuProAlaPheGlyTrpValValLeuAlaPheArgAlaAspAsnProGly 497

GCCTGGCTGTTCCACTGCCACATGCCCTGGCACGTCTCGGGCGTCGTCTACCTCGAGCGCCGACGACCT          2880
AlaTrpLeuPheHisCysHisIleAlaTrpHisValSerGlyValValTyrLeuGluArgAlaAspLe            524

GCGCGGGGCCCGTCTCGGACGCCGACCTCTGCGCCGACTGGCGCCTACTGGCCTACCAACC                  2960
uArgGlyAlaValSerAspAlaAspAlaAspProArgLeuCysAlaAspTrpArgArgTyrTrpProThrAsnP      551

CCTACCCCAAGTCCGACTCGGCCTCAAGCACCGCTGGGTGCGAGGAGGGCGAGTGGTGTCAAGGCGtgagcgaaggag 3040
roTyrProLysSerAspSerGlyLeuLysHisArgTrpValGluGlyGluTrpLeuValLysAla***
```

Fig. 7E gaaaaaggaaacaaagaggggggggctagttcctatttttgcttttttgtcttgtccttgtgctggcggt 3120 tacctggtaaaggagaaggggccccaagttcgagtggtgtgatcgggtaaatattatcaagagatct 3192

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
GTCGTCTACC TCGAGCGCGC C                                                    21

(2) INFORMATION FOR SEQ ID NO:2:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

GTCATCTAGA CGCTCACGCC TTGACCAGCC A                                         31

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GTAGACGACG CCGAAGCCGC CCGAGAC                                              27

(2) INFORMATION FOR SEQ ID NO:4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GACGACGCCC AGGCCAGCCT CGAGGTGCCA GGCGATGTG                                 39

(2) INFORMATION FOR SEQ ID NO:5:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GAGGTAGACG ACGCCGAAGC CAGCCTCGAG GTGCCAGGCG ATGTG                          45

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CGGTACCGTC TAGAGTCGCG ATGCATC                                              27

(2) INFORMATION FOR SEQ ID NO:7:
```

(i) SEQUENCE CHARACTERISTICS:
    (A) LENGTH: 35 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:7:

CCGGGCCATG GCAGATCTCA GCGCTACGTA GGATC        35

(2) INFORMATION FOR SEQ ID NO:8:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

ATGATGAAGT CCTTCATCAG CGCCGCGACG CTTTTGGTGG G        41

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

TACTACTTCA GGAAGTAGTC GCGGCGCTGC GAAAACCAC        39

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GGGTCTAGAG GTGACTGACA CCTGGCGGT        29

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

TGACCCGGGA ACTGGCCCCG ACATTCCAGC        30

(2) INFORMATION FOR SEQ ID NO:12:

(i) SEQUENCE CHARACTERISTICS:
        (A) LENGTH: 32 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:12:

GGGATTTAAA TATGAAGTCC TTCATCAGCG CC                           32

(2) INFORMATION FOR SEQ ID NO:13:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

GGGTTAATTA ATTACGCCTT GACCAGCCAC TCGCC                        35

(2) INFORMATION FOR SEQ ID NO:14:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:14:

ATACACAACT GGATGATGAA GTCCTTCATC AGCG                         34

(2) INFORMATION FOR SEQ ID NO:15:

(i) SEQUENCE CHARACTERISTICS:
            (A) LENGTH: 117 base pairs
            (B) TYPE: nucleic acid
            (C) STRANDEDNESS: single
            (D) TOPOLOGY: linear (xi) SEQUENCE DESCRIPTION: SEQ ID NO:15:

AATTCGTCGA CGGCTCTATT TCTGTACGGC CTTCAGGTGG CCGCACCGGC CATGCATAGC    60

AGCTGCCAGA GATAAAGACA TGCCGGAAGT CCACCGGCGT GGCCGGTACG TATTCGA      117

(2) INFORMATION FOR SEQ ID NO:16:

(i) SEQUENCE CHARACTERISTICS:
            (A) LENGTH: 88 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:16:

AATTGTTTAA ACTCTAGAGA ATTCAAGCTT GTCGACGTTT AAACCAAATT TGAGATCTCT    60

TAAGTTCGAA CAGCTGCAAA TTTGTCGA                                      88

(2) INFORMATION FOR SEQ ID NO:17:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:17:

ATGCATAGGG TGGAGAGTAT ATGATGG                                                        27

(2) INFORMATION FOR SEQ ID NO:18:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:18:

CTGAATTCCG TTTCGTTTAC                                                                20

(2) INFORMATION FOR SEQ ID NO:19:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:19:

TCCTGCAGAA TGCAATTTAA ACTC                                                           24

(2) INFORMATION FOR SEQ ID NO:20:

(i) SEQUENCE CHARACTERISTICS:
             (A) LENGTH: 36 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:20:

CTATGCATAT TTAAATGCCT TCTGTGGGGT TTATTG                                              36

(2) INFORMATION FOR SEQ ID NO:21:

(i) SEQUENCE CHARACTERISTICS:
             (A) LENGTH: 15 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:21:

AATTGGGCCC ATGCA                                                                     15

(2) INFORMATION FOR SEQ ID NO:22:

(i) SEQUENCE CHARACTERISTICS:
             (A) LENGTH: 39 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:22:

CACATTGACT GGCACTTGGA GGCTGGGCTC GCACTTGTC                                           39

(2) INFORMATION FOR SEQ ID NO:23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

```
CTTGGAGGCT GGGTTCGCAC TTGTC                                     25
```

(2) INFORMATION FOR SEQ ID NO:24:

(i) SEQUENCE CHARACTERISTICS:
        (A) LENGTH: 1588 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1587

(xi) SEQUENCE DESCRIPTION: SEQ ID NO:24:

```
ATG CTT TCT AGC ATT ACC CTC CTA CCT TTG CTC GCT GCG GTC TCA ACC    48
Met Leu Ser Ser Ile Thr Leu Leu Pro Leu Leu Ala Ala Val Ser Thr
  1               5                  10                  15

CCC GCC TTT GCT GCC GTC CGC AAC TAT AAG TTC GAC ATC AAG AAC GTC    96
Pro Ala Phe Ala Ala Val Arg Asn Tyr Lys Phe Asp Ile Lys Asn Val
             20                  25                  30

AAT GTC GCT CCC GAT GGC TTT CAG CGC TCT ATC GTC TCC GTC AAC GGT   144
Asn Val Ala Pro Asp Gly Phe Gln Arg Ser Ile Val Ser Val Asn Gly
         35                  40                  45

TTA GTT CCT GGC ACG TTG ATC ACG GCC AAC AAG GGT GAC ACC TTG CGC   192
Leu Val Pro Gly Thr Leu Ile Thr Ala Asn Lys Gly Asp Thr Leu Arg
     50                  55                  60

ATT AAT GTC ACG AAT CAA CTC ACG GAC CCT AGT ATG CGT CGT GCC ACA   240
Ile Asn Val Thr Asn Gln Leu Thr Asp Pro Ser Met Arg Arg Ala Thr
 65                  70                  75                  80

ACG ATT CAT TGG CAT GGA TTG TTC CAA GCT ACT ACC GCC GAC GAG GAT   288
Thr Ile His Trp His Gly Leu Phe Gln Ala Thr Thr Ala Asp Glu Asp
                 85                  90                  95

GGC CCC GCA TTC GTC ACG CAA TGC CCT ATT GCG CAA AAT TTG TCC TAT   336
Gly Pro Ala Phe Val Thr Gln Cys Pro Ile Ala Gln Asn Leu Ser Tyr
            100                 105                 110

ACA TAC GAG ATC CCA TTG CGC GGC CAA ACA GGA ACC ATG TGG TAT CAC   384
Thr Tyr Glu Ile Pro Leu Arg Gly Gln Thr Gly Thr Met Trp Tyr His
        115                 120                 125

GCC CAT CTT GCG AGT CAA TAT GTC GAT GGA TTG CGA GGC CCT TTG GTC   432
Ala His Leu Ala Ser Gln Tyr Val Asp Gly Leu Arg Gly Pro Leu Val
    130                 135                 140

ATC TAT GAT CCA AAC GAC CCA CAC AAG TCG CGC TAC GAC GTG GAT GAT   480
Ile Tyr Asp Pro Asn Asp Pro His Lys Ser Arg Tyr Asp Val Asp Asp
145                 150                 155                 160

GCG AGC ACA GTA GTC ATG CTT GAG GAC TGG TAC CAT ACT CCG GCA CCC   528
Ala Ser Thr Val Val Met Leu Glu Asp Trp Tyr His Thr Pro Ala Pro
                165                 170                 175

GTT CTA GAA AAG CAA ATG TTC TCG ACT AAT AAC ACC GCT CTG CTC TCT   576
Val Leu Glu Lys Gln Met Phe Ser Thr Asn Asn Thr Ala Leu Leu Ser
            180                 185                 190
```

| | | |
|---|---|---|
| CCT GTT CCG GAC TCG GGT CTT ATC AAT GGC AAA GGG CGC TAT GTG GGC<br>Pro Val Pro Asp Ser Gly Leu Ile Asn Gly Lys Gly Arg Tyr Val Gly<br>195 200 205 | 624 | |
| GGT CCC GCA GTT CCC CGG TCA GTA ATC AAC GTA AAA CGT GGG AAA CGA<br>Gly Pro Ala Val Pro Arg Ser Val Ile Asn Val Lys Arg Gly Lys Arg<br>210 215 220 | 672 | |
| TAT CGC TTG CGC GTA ATC AAC GCT TCT GCT ATC GGG TCG TTT ACC TTT<br>Tyr Arg Leu Arg Val Ile Asn Ala Ser Ala Ile Gly Ser Phe Thr Phe<br>225 230 235 240 | 720 | |
| TCG ATC GAA GGA CAT AGT CTG ACT GTC ATT GAG GCC GAT GGG ATC CTG<br>Ser Ile Glu Gly His Ser Leu Thr Val Ile Glu Ala Asp Gly Ile Leu<br>245 250 255 | 768 | |
| CAC CAG CCC TTG GCT GTT GAC AGC TTC CAG ATT TAC GCT GGA CAA CGC<br>His Gln Pro Leu Ala Val Asp Ser Phe Gln Ile Tyr Ala Gly Gln Arg<br>260 265 270 | 816 | |
| TAC TCT GTC ATC GTT GAA GCC AAC CAA ACC GCC GCC AAC TAC TGG ATT<br>Tyr Ser Val Ile Val Glu Ala Asn Gln Thr Ala Ala Asn Tyr Trp Ile<br>275 280 285 | 864 | |
| CGT GCA CCA ATG ACC GTT GCA GGA GCC GGA ACC AAT GCA AAC TTG GAC<br>Arg Ala Pro Met Thr Val Ala Gly Ala Gly Thr Asn Ala Asn Leu Asp<br>290 295 300 | 912 | |
| CCC ACC AAT GTC TTT GCC GTA TTG CAC TAC GAG GGA GCG CCC AAC GCC<br>Pro Thr Asn Val Phe Ala Val Leu His Tyr Glu Gly Ala Pro Asn Ala<br>305 310 315 320 | 960 | |
| GAA CCC ACG ACG GAA CAA GGC AGT GCT ATC GGT ACT GCA CTC GTT GAA<br>Glu Pro Thr Thr Glu Gln Gly Ser Ala Ile Gly Thr Ala Leu Val Glu<br>325 330 335 | 1008 | |
| GAG AAC CTC CAT GCG CTC ATC AAC CCT GGC GCT CCG GGC GGC TCC GCT<br>Glu Asn Leu His Ala Leu Ile Asn Pro Gly Ala Pro Gly Gly Ser Ala<br>340 345 350 | 1056 | |
| CCC GCA GAC GTT TCC CTC AAT CTT GCA ATT GGG CGC AGC ACA GTT GAT<br>Pro Ala Asp Val Ser Leu Asn Leu Ala Ile Gly Arg Ser Thr Val Asp<br>355 360 365 | 1104 | |
| GGG ATT CTT AGG TTC ACA TTT AAT AAC ATC AAG TAC GAG GCT CCT TCG<br>Gly Ile Leu Arg Phe Thr Phe Asn Asn Ile Lys Tyr Glu Ala Pro Ser<br>370 375 380 | 1152 | |
| TTG CCC ACG CTC TTG AAG ATT TTG GCA AAC AAT GCG AGC AAT GAC GCC<br>Leu Pro Thr Leu Leu Lys Ile Leu Ala Asn Asn Ala Ser Asn Asp Ala<br>385 390 395 400 | 1200 | |
| GAT TTC ACG CCA AAT GAG CAC ACT ATC GTA TTG CCA CAC AAT AAA GTT<br>Asp Phe Thr Pro Asn Glu His Thr Ile Val Leu Pro His Asn Lys Val<br>405 410 415 | 1248 | |
| ATC GAG CTC AAT ATC ACC GGA GGT GCA GAC CAC CCT ATC CAT CTC CAC<br>Ile Glu Leu Asn Ile Thr Gly Gly Ala Asp His Pro Ile His Leu His<br>420 425 430 | 1296 | |
| GGC CAT GTG TTT GAT ATC GTC AAA TCA CTC GGT GGT ACC CCG AAC TAT<br>Gly His Val Phe Asp Ile Val Lys Ser Leu Gly Gly Thr Pro Asn Tyr<br>435 440 445 | 1344 | |
| GTC AAC CCG CCA CGC AGG GAC GTA GTT CGT GTC GGA GGC ACC GGT GTG<br>Val Asn Pro Pro Arg Arg Asp Val Val Arg Val Gly Gly Thr Gly Val<br>450 455 460 | 1392 | |
| GTA CTC CGA TTC AAG ACC GAT AAC CCA GGC CCA TGG TTT GTT CAC TGC<br>Val Leu Arg Phe Lys Thr Asp Asn Pro Gly Pro Trp Phe Val His Cys<br>465 470 475 480 | 1440 | |
| CAC ATT GAC TGG CAC TTG GAG GCT GGG CTC GCA CTT GTC TTT GCC GAG<br>His Ile Asp Trp His Leu Glu Ala Gly Leu Ala Leu Val Phe Ala Glu<br>485 490 495 | 1488 | |
| GCC CCC AGC CAG ATT CGC CAG GGT GTC CAG TCG GTC CAG CCC AAC AAT<br>Ala Pro Ser Gln Ile Arg Gln Gly Val Gln Ser Val Gln Pro Asn Asn<br>500 505 510 | 1536 | |

```
GCC TGG AAC CAG CTC TGC CCC AAG TAC GCG GCT CTT CCT CCC GAT TTG       1584
Ala Trp Asn Gln Leu Cys Pro Lys Tyr Ala Ala Leu Pro Pro Asp Leu
        515                 520                 525

CAG T                                                                 1588
Gln
```

(2) INFORMATION FOR SEQ ID NO:25:

(i) SEQUENCE CHARACTERISTICS:
        (A) LENGTH: 529 amino acids
        (B) TYPE: amino acid
        (D) TOPOLOGY: linear (ii) MOLECULE TYPE: protein (xi) SEQUENCE DESCRIPTION: SEQ ID NO:25:

```
Met Leu Ser Ser Ile Thr Leu Leu Pro Leu Leu Ala Ala Val Ser Thr
 1               5                  10                  15

Pro Ala Phe Ala Ala Val Arg Asn Tyr Lys Phe Asp Ile Lys Asn Val
            20                  25                  30

Asn Val Ala Pro Asp Gly Phe Gln Arg Ser Ile Val Ser Val Asn Gly
        35                  40                  45

Leu Val Pro Gly Thr Leu Ile Thr Ala Asn Lys Gly Asp Thr Leu Arg
    50                  55                  60

Ile Asn Val Thr Asn Gln Leu Thr Asp Pro Ser Met Arg Arg Ala Thr
65                  70                  75                  80

Thr Ile His Trp His Gly Leu Phe Gln Ala Thr Thr Ala Asp Glu Asp
                85                  90                  95

Gly Pro Ala Phe Val Thr Gln Cys Pro Ile Ala Gln Asn Leu Ser Tyr
            100                 105                 110

Thr Tyr Glu Ile Pro Leu Arg Gly Gln Thr Gly Thr Met Trp Tyr His
        115                 120                 125

Ala His Leu Ala Ser Gln Tyr Val Asp Gly Leu Arg Gly Pro Leu Val
    130                 135                 140

Ile Tyr Asp Pro Asn Asp Pro His Lys Ser Arg Tyr Asp Val Asp Asp
145                 150                 155                 160

Ala Ser Thr Val Val Met Leu Glu Asp Trp Tyr His Thr Pro Ala Pro
                165                 170                 175

Val Leu Glu Lys Gln Met Phe Ser Thr Asn Asn Thr Ala Leu Leu Ser
            180                 185                 190

Pro Val Pro Asp Ser Gly Leu Ile Asn Gly Lys Gly Arg Tyr Val Gly
        195                 200                 205

Gly Pro Ala Val Pro Arg Ser Val Ile Asn Val Lys Arg Gly Lys Arg
    210                 215                 220

Tyr Arg Leu Arg Val Ile Asn Ala Ser Ala Ile Gly Ser Phe Thr Phe
225                 230                 235                 240

Ser Ile Glu Gly His Ser Leu Thr Val Ile Glu Ala Asp Gly Ile Leu
                245                 250                 255

His Gln Pro Leu Ala Val Asp Ser Phe Gln Ile Tyr Ala Gly Gln Arg
            260                 265                 270

Tyr Ser Val Ile Val Glu Ala Asn Gln Thr Ala Ala Asn Tyr Trp Ile
        275                 280                 285

Arg Ala Pro Met Thr Val Ala Gly Ala Gly Thr Asn Ala Asn Leu Asp
    290                 295                 300

Pro Thr Asn Val Phe Ala Val Leu His Tyr Glu Gly Ala Pro Asn Ala
305                 310                 315                 320

Glu Pro Thr Thr Glu Gln Gly Ser Ala Ile Gly Thr Ala Leu Val Glu
```

```
                       325                 330                 335
Glu Asn Leu His Ala Leu Ile Asn Pro Gly Ala Pro Gly Gly Ser Ala
            340                 345                 350
Pro Ala Asp Val Ser Leu Asn Leu Ala Ile Gly Arg Ser Thr Val Asp
        355                 360                 365
Gly Ile Leu Arg Phe Thr Phe Asn Asn Ile Lys Tyr Glu Ala Pro Ser
    370                 375                 380
Leu Pro Thr Leu Leu Lys Ile Leu Ala Asn Asn Ala Ser Asn Asp Ala
385                 390                 395                 400
Asp Phe Thr Pro Asn Glu His Thr Ile Val Leu Pro His Asn Lys Val
                405                 410                 415
Ile Glu Leu Asn Ile Thr Gly Gly Ala Asp His Pro Ile His Leu His
            420                 425                 430
Gly His Val Phe Asp Ile Val Lys Ser Leu Gly Gly Thr Pro Asn Tyr
        435                 440                 445
Val Asn Pro Pro Arg Arg Asp Val Val Arg Val Gly Gly Thr Gly Val
    450                 455                 460
Val Leu Arg Phe Lys Thr Asp Asn Pro Gly Pro Trp Phe Val His Cys
465                 470                 475                 480
His Ile Asp Trp His Leu Glu Ala Gly Leu Ala Leu Val Phe Ala Glu
                485                 490                 495
Ala Pro Ser Gln Ile Arg Gln Gly Val Gln Ser Val Gln Pro Asn Asn
            500                 505                 510
Ala Trp Asn Gln Leu Cys Pro Lys Tyr Ala Ala Leu Pro Pro Asp Leu
        515                 520                 525
Gln
```

(2) INFORMATION FOR SEQ ID NO:26:

(i) SEQUENCE CHARACTERISTICS:
        (A) LENGTH: 3192 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(587..832, 918..995, 1080..1091, 1194..1265,
            1338..2309, 2457..2525, 2619..3029)

(xi) SEQUENCE DESCRIPTION: SEQ ID NO:26:

```
GCTAGCTTCT TTGGTCACCG TCGTTTTCGC CCGCCCCCTC CCTCCTTCAA CCCCCTGAGT    60

AGTCGGCTAA GCGATCCTCA ATCTGGTCTT GTGAGGTCAC GTCCTCCAGC AGATGACAGT   120

TCATCGAGCG AGTGATCTCC ACCACCCAGA AGGGAGGGGG GATGCGCGCA TGCTCCAACA   180

TACCCTGGTG TCGCTAGAGA CGTCGCGGCA TCAGCCTTTT CATCACACCG AGCACGTCCA   240

CGGACCGGCT CCTTTCACCC CCGCGTCCTC CGGAGGATTG AGTCACGATA TTTCGGGATG   300

TGGGAAGGGG GAGAGAAAGG AGGGGGGAGG GGCGGAAACA TGTTGGATAC GAGCTGCGCC   360

CCTTTTCCAA CATCGAGAAC AGGAAGTCGT TGGTGTCGGC CGTAATGTCT ATAAAACGAG   420

GCTCCTTCTC GTCGTCGACT TGTCTCAGGT TCTCTCTCTC GTCCACACCA AGCCAGTCTT   480

GCCTGAGCCA CCTGAGCCAC CTTCAACTCA TCATCTTCAG TCAAGTCGTT CATTGACATT   540

GTGTCTCTCT TTCTATCGAG TCGGCTTCCC GGCCCTTCAC CACAAC ATG AAG TCC      595
                                                Met Lys Ser
                                                  1
```

| | |
|---|---:|
| TTC ATC AGC GCC GCG ACG CTT TTG GTG GGC ATT CTC ACC CCT AGC GTT<br>Phe Ile Ser Ala Ala Thr Leu Leu Val Gly Ile Leu Thr Pro Ser Val<br>     5                   10                   15 | 643 |
| GCT GCT GCC CCT CCA TCC ACC CCT GAG CAG CGC GAC CTG CTC GTC CCG<br>Ala Ala Ala Pro Pro Ser Thr Pro Glu Gln Arg Asp Leu Leu Val Pro<br> 20                  25                   30                   35 | 691 |
| ATC ACG GAG AGG GAG GAG GCA GCC GTG AAG GCT CGC CAG CAG AGC TGC<br>Ile Thr Glu Arg Glu Glu Ala Ala Val Lys Ala Arg Gln Gln Ser Cys<br>              40                   45                   50 | 739 |
| AAC ACC CCC AGC AAC CGG GCG TGC TGG ACT GAC GGA TAC GAC ATC AAC<br>Asn Thr Pro Ser Asn Arg Ala Cys Trp Thr Asp Gly Tyr Asp Ile Asn<br>         55                   60                   65 | 787 |
| ACC GAC TAC GAA GTG GAC AGC CCG GAC ACG GGT GTT GTT CGG CCG<br>Thr Asp Tyr Glu Val Asp Ser Pro Asp Thr Gly Val Val Arg Pro<br>         70                   75                   80 | 832 |
| GTGAGTGCTC TCGTTAATTA CGCTTCGGCG AGTTGCGCAG ATATATTAAA TACTGCAAAC | 892 |
| CTAAGCAGGA GCTGACATGC GACAG TAC ACT CTG ACT CTC ACC GAA GTC GAC<br>                                                  Tyr Thr Leu Thr Leu Thr Glu Val Asp<br>                                                        85                   90 | 944 |
| AAC TGG ACC GGA CCT GAT GGC GTC GTC AAG GAG AAG GTC ATG CTG GTT<br>Asn Trp Thr Gly Pro Asp Gly Val Val Lys Glu Lys Val Met Leu Val<br>         95                   100                   105 | 992 |
| AAC GTACGGCACC CCTTTTCTTG TCCTAGGATC TGGGTGATGT GCGTCGTTGC<br>Asn | 1045 |
| CCCTGAGAGA GACTGACCGA GCCTTTGGCT GCAG AAT AGT ATA ATC GTAATTAATT<br>                                                           Asn Ser Ile Ile<br>                                                               110 | 1101 |
| ATACCGCCCT GCCTCCAGCA GCCCCAGCAG CTCGAGAAGG GTATCTGAAG TTAGTCAGGC | 1161 |
| CTGCTGACCT GACCGGGGCC AACCCACCAT AG GGA CCA ACA ATC TTT GCG GAC<br>                                                    Gly Pro Thr Ile Phe Ala Asp<br>                                                               115 | 1214 |
| TGG GGC GAC ACG ATC CAG GTA ACG GTC ATC AAC AAC CTC GAG ACC AAC<br>Trp Gly Asp Thr Ile Gln Val Thr Val Ile Asn Asn Leu Glu Thr Asn<br>120                   125                   130                   135 | 1262 |
| GGC GTATGTCTGC TGCTTGCTCT CTTGCTCTCC TCGTCCGCGA CTAATAATAA<br>Gly | 1315 |
| TATCAACTCG TGTGGAAAAC AG ACG TCG ATC CAC TGG CAC GGA CTG CAC CAG<br>                                   Thr Ser Ile His Trp His Gly Leu His Gln<br>                                             140                   145 | 1367 |
| AAG GGC ACC AAC CTG CAC GAC GGC GCC AAC GGT ATC ACC GAG TGC CCG<br>Lys Gly Thr Asn Leu His Asp Gly Ala Asn Gly Ile Thr Glu Cys Pro<br>         150                   155                   160 | 1415 |
| ATC CCC CCC AAG GGA GGG AGG AAG GTG TAC CGG TTC AAG GCT CAG CAG<br>Ile Pro Pro Lys Gly Gly Arg Lys Val Tyr Arg Phe Lys Ala Gln Gln<br>         165                   170                   175 | 1463 |
| TAC GGG ACG AGC TGG TAC CAC TCG CAC TTC TCG GCC CAG TAC GGC AAC<br>Tyr Gly Thr Ser Trp Tyr His Ser His Phe Ser Ala Gln Tyr Gly Asn<br>         180                   185                   190 | 1511 |
| GGC GTG GTC GGG GCC ATT CAG ATC AAC GGA CCG GCC TCG CTG CCG TAC<br>Gly Val Val Gly Ala Ile Gln Ile Asn Gly Pro Ala Ser Leu Pro Tyr<br>195                   200                   205                   210 | 1559 |
| GAC ACC GAC CTG GGT GTG TTC CCC ATC AGC GAC TAC TAC TAC AGC TCG<br>Asp Thr Asp Leu Gly Val Phe Pro Ile Ser Asp Tyr Tyr Tyr Ser Ser<br>              215                   220                   225 | 1607 |
| GCC GAC GAG CTG GTG GAA CTC ACC AAG AAC TCG GGC GCG CCC TTC AGC<br>Ala Asp Glu Leu Val Glu Leu Thr Lys Asn Ser Gly Ala Pro Phe Ser<br>         230                   235                   240 | 1655 |
| GAC AAC GTC CTG TTC AAC GGC ACG GCC AAG CAC CCG GAG ACG GGC GAG<br>Asp Asn Val Leu Phe Asn Gly Thr Ala Lys His Pro Glu Thr Gly Glu | 1703 |

```
                       245                   250                      255
GGC GAG TAC GCC AAC GTG ACG CTC ACC CCG GGC CGG CGG CAC CGC CTG           1751
Gly Glu Tyr Ala Asn Val Thr Leu Thr Pro Gly Arg Arg His Arg Leu
    260                 265                 270

CGC CTG ATC AAC ACG TCG GTC GAG AAC CAC TTC CAG GTC TCG CTC GTC           1799
Arg Leu Ile Asn Thr Ser Val Glu Asn His Phe Gln Val Ser Leu Val
275                 280                 285                 290

AAC CAC ACC ATG TGC ATC ATC GCC GCC GAC ATG GTG CCC GTC AAC GCC           1847
Asn His Thr Met Cys Ile Ile Ala Ala Asp Met Val Pro Val Asn Ala
                295                 300                 305

ATG ACG GTC GAC AGC CTC TTC CTC GGC GTC GGC CAG CGT TAC GAT GTC           1895
Met Thr Val Asp Ser Leu Phe Leu Gly Val Gly Gln Arg Tyr Asp Val
            310                 315                 320

GTC ATC GAA GCC AAC CGA ACG CCC GGG AAC TAC TGG TTT AAC GTC ACA           1943
Val Ile Glu Ala Asn Arg Thr Pro Gly Asn Tyr Trp Phe Asn Val Thr
        325                 330                 335

TTT GGC GGC GGC CTG CTC TGC GGC GGC TCC AGG AAT CCC TAC CCG GCC           1991
Phe Gly Gly Gly Leu Leu Cys Gly Gly Ser Arg Asn Pro Tyr Pro Ala
    340                 345                 350

GCC ATC TTC CAC TAC GCC GGC GCC CCC GGC GGC CCG CCC ACG GAC GAG           2039
Ala Ile Phe His Tyr Ala Gly Ala Pro Gly Gly Pro Pro Thr Asp Glu
355                 360                 365                 370

GGC AAG GCC CCG GTC GAC CAC AAC TGC CTG GAC CTC CCC AAC CTC AAG           2087
Gly Lys Ala Pro Val Asp His Asn Cys Leu Asp Leu Pro Asn Leu Lys
                375                 380                 385

CCC GTC GTG GCC CGC GAC GTG CCC CTG AGC GGC TTC GCC AAG CGG GCC           2135
Pro Val Val Ala Arg Asp Val Pro Leu Ser Gly Phe Ala Lys Arg Ala
            390                 395                 400

GAC AAC ACG CTC GAC GTC ACC CTC GAC ACC ACG GGC ACG CCC CTG TTC           2183
Asp Asn Thr Leu Asp Val Thr Leu Asp Thr Thr Gly Thr Pro Leu Phe
        405                 410                 415

GTC TGG AAG GTC AAC GGC AGC GCC ATC AAC ATC GAC TGG GGG AGG GCC           2231
Val Trp Lys Val Asn Gly Ser Ala Ile Asn Ile Asp Trp Gly Arg Ala
    420                 425                 430

GTC GTC GAC TAC GTC CTC ACG CAG AAC ACC AGC TTC CCA CCC GGG TAC           2279
Val Val Asp Tyr Val Leu Thr Gln Asn Thr Ser Phe Pro Pro Gly Tyr
435                 440                 445                 450

AAC ATT GTC GAG GTG AAC GGA GCT GAT CAG GTAAGAAAAA GGGGACCGCA             2329
Asn Ile Val Glu Val Asn Gly Ala Asp Gln
                455                 460

GGGGTGCTGC TGCAAGTACA CCTTGCTCGC CCTCCTGTTC TTCCTTAATA ACTACCTCCC         2389

AACCCTCCCC CCTAATTAAT TCACTTTAAA GGCCGATCAA GACTGACCGA GCCCCCTCTC         2449

TTTGCAG TGG TCG TAC TGG TTG ATC GAG AAC GAT CCC GGC GCA CCT TTC           2498
        Trp Ser Tyr Trp Leu Ile Glu Asn Asp Pro Gly Ala Pro Phe
                            465                 470

ACC CTA CCG CAT CCG ATG CAC CTG CAC GTAAGTTGGA TACATATATA                 2545
Thr Leu Pro His Pro Met His Leu His
475                 480

TATATATATA TACATTGCTT TCCTGGCTCG CTCCCTTAAA TAAAATTAAA TAACCAAAAA         2605

TAACAAAAAA AAG GGC CAC GAC TTT TAC GTG CTG GGC CGC TCG CCC GAC           2654
            Gly His Asp Phe Tyr Val Leu Gly Arg Ser Pro Asp
                    485                 490                 495

GAG TCG CCG GCA TCC AAC GAG CGG CAC GTG TTC GAT CCG GCG CGG GAC           2702
Glu Ser Pro Ala Ser Asn Glu Arg His Val Phe Asp Pro Ala Arg Asp
                500                 505                 510

GCG GGC CTG CTG AGC GGG GCC AAC CCT GTG CGG CGG GAC GTG TCG ATG           2750
Ala Gly Leu Leu Ser Gly Ala Asn Pro Val Arg Arg Asp Val Ser Met
            515                 520                 525
```

| | | | | |
|---|---|---|---|---|
| CTG CCG GCG TTC GGG TGG GTG GTG CTG TCC TTC CGG GCC GAC AAC CCG | | | | 2798 |
| Leu Pro Ala Phe Gly Trp Val Val Leu Ser Phe Arg Ala Asp Asn Pro | | | | |
| 530 535 540 | | | | |
| GGC GCC TGG CTG TTC CAC TGC CAC ATC GCC TGG CAC GTC TCG GGC GGC | | | | 2846 |
| Gly Ala Trp Leu Phe His Cys His Ile Ala Trp His Val Ser Gly Gly | | | | |
| 545 550 555 | | | | |
| CTG GGC GTC GTC TAC CTC GAG CGC GCC GAC GAC CTG CGC GGG GCC GTC | | | | 2894 |
| Leu Gly Val Val Tyr Leu Glu Arg Ala Asp Asp Leu Arg Gly Ala Val | | | | |
| 560 565 570 575 | | | | |
| TCG GAC GCC GAC GCC GAC GAC CTC GAC CGC CTC TGC GCC GAC TGG CGC | | | | 2942 |
| Ser Asp Ala Asp Ala Asp Asp Leu Asp Arg Leu Cys Ala Asp Trp Arg | | | | |
| 580 585 590 | | | | |
| CGC TAC TGG CCT ACC AAC CCC TAC CCC AAG TCC GAC TCG GGC CTC AAA | | | | 2990 |
| Arg Tyr Trp Pro Thr Asn Pro Tyr Pro Lys Ser Asp Ser Gly Leu Lys | | | | |
| 595 600 605 | | | | |
| CAC CGC TGG GTC GAG GAG GGC GAG TGG CTG GTC AAG GCG TGAGCGAAGG | | | | 3039 |
| His Arg Trp Val Glu Glu Gly Glu Trp Leu Val Lys Ala | | | | |
| 610 615 620 | | | | |
| AGGAAAAAGG AAACAAAGAG GGGGGGGGGG GCTAGTTCCT ATTTTTGCTT TTTTTTTTTG | | | | 3099 |
| TTCTTGTCCT TGTGCTGGCG GTTCCCTGGT AAAGGAGAAG GGGGCCCCAA GTTCGAGTGG | | | | 3159 |
| GTGTGTGATC GGGTAAATAT TATCAAGAGA TCT | | | | 3192 |

(2) INFORMATION FOR SEQ ID NO:27:

(i) SEQUENCE CHARACTERISTICS:
        (A) LENGTH: 620 amino acids
        (B) TYPE: amino acid
        (D) TOPOLOGY: linear (ii) MOLECULE TYPE: protein (xi) SEQUENCE DESCRIPTION: SEQ ID NO:27:

Met Lys Ser Phe Ile Ser Ala Ala Thr Leu Leu Val Gly Ile Leu Thr
1               5                   10                  15

Pro Ser Val Ala Ala Pro Pro Ser Thr Pro Glu Gln Arg Asp Leu
            20                  25                  30

Leu Val Pro Ile Thr Glu Arg Glu Ala Ala Val Lys Ala Arg Gln
        35                  40                  45

Gln Ser Cys Asn Thr Pro Ser Asn Arg Ala Cys Trp Thr Asp Gly Tyr
50                  55                  60

Asp Ile Asn Thr Asp Tyr Glu Val Asp Ser Pro Asp Thr Gly Val Val
65                  70                  75                  80

Arg Pro Tyr Thr Leu Thr Leu Thr Glu Val Asp Asn Trp Thr Gly Pro
            85                  90                  95

Asp Gly Val Val Lys Glu Lys Val Met Leu Val Asn Asn Ser Ile Ile
            100                 105                 110

Gly Pro Thr Ile Phe Ala Asp Trp Gly Asp Thr Ile Gln Val Thr Val
            115                 120                 125

Ile Asn Asn Leu Glu Thr Asn Gly Thr Ser Ile His Trp His Gly Leu
130                 135                 140

His Gln Lys Gly Thr Asn Leu His Asp Gly Ala Asn Gly Ile Thr Glu
145                 150                 155                 160

Cys Pro Ile Pro Pro Lys Gly Gly Arg Lys Val Tyr Arg Phe Lys Ala
                165                 170                 175

Gln Gln Tyr Gly Thr Ser Trp Tyr His Ser His Phe Ser Ala Gln Tyr
            180                 185                 190

Gly Asn Gly Val Val Gly Ala Ile Gln Ile Asn Gly Pro Ala Ser Leu
            195                 200                 205

-continued

Pro Tyr Asp Thr Asp Leu Gly Val Phe Pro Ile Ser Asp Tyr Tyr Tyr
    210                 215                 220

Ser Ser Ala Asp Glu Leu Val Glu Leu Thr Lys Asn Ser Gly Ala Pro
225             230                 235                 240

Phe Ser Asp Asn Val Leu Phe Asn Gly Thr Ala Lys His Pro Glu Thr
            245                 250                 255

Gly Glu Gly Glu Tyr Ala Asn Val Thr Leu Thr Pro Gly Arg Arg His
        260                 265                 270

Arg Leu Arg Leu Ile Asn Thr Ser Val Glu Asn His Phe Gln Val Ser
    275                 280                 285

Leu Val Asn His Thr Met Cys Ile Ile Ala Ala Asp Met Val Pro Val
290             295                 300

Asn Ala Met Thr Val Asp Ser Leu Phe Leu Gly Val Gly Gln Arg Tyr
305             310                 315                 320

Asp Val Val Ile Glu Ala Asn Arg Thr Pro Gly Asn Tyr Trp Phe Asn
                325                 330                 335

Val Thr Phe Gly Gly Gly Leu Leu Cys Gly Gly Ser Arg Asn Pro Tyr
            340                 345                 350

Pro Ala Ala Ile Phe His Tyr Ala Gly Ala Pro Gly Gly Pro Pro Thr
                355                 360                 365

Asp Glu Gly Lys Ala Pro Val Asp His Asn Cys Leu Asp Leu Pro Asn
    370                 375                 380

Leu Lys Pro Val Val Ala Arg Asp Val Pro Leu Ser Gly Phe Ala Lys
385                 390                 395                 400

Arg Ala Asp Asn Thr Leu Asp Val Thr Leu Asp Thr Thr Gly Thr Pro
                405                 410                 415

Leu Phe Val Trp Lys Val Asn Gly Ser Ala Ile Asn Ile Asp Trp Gly
            420                 425                 430

Arg Ala Val Val Asp Tyr Val Leu Thr Gln Asn Thr Ser Phe Pro Pro
                435                 440                 445

Gly Tyr Asn Ile Val Glu Val Asn Gly Ala Asp Gln Trp Ser Tyr Trp
    450                 455                 460

Leu Ile Glu Asn Asp Pro Gly Ala Pro Phe Thr Leu Pro His Pro Met
465                 470                 475                 480

His Leu His Gly His Asp Phe Tyr Val Leu Gly Arg Ser Pro Asp Glu
                485                 490                 495

Ser Pro Ala Ser Asn Glu Arg His Val Phe Asp Pro Ala Arg Asp Ala
            500                 505                 510

Gly Leu Leu Ser Gly Ala Asn Pro Val Arg Arg Asp Val Ser Met Leu
                515                 520                 525

Pro Ala Phe Gly Trp Val Val Leu Ser Phe Arg Ala Asp Asn Pro Gly
    530                 535                 540

Ala Trp Leu Phe His Cys His Ile Ala Trp His Val Ser Gly Gly Leu
545                 550                 555                 560

Gly Val Val Tyr Leu Glu Arg Ala Asp Asp Leu Arg Gly Ala Val Ser
                565                 570                 575

Asp Ala Asp Ala Asp Asp Leu Asp Arg Leu Cys Ala Asp Trp Arg Arg
            580                 585                 590

Tyr Trp Pro Thr Asn Pro Tyr Pro Lys Ser Asp Ser Gly Leu Lys His
        595                 600                 605

Arg Trp Val Glu Glu Gly Glu Trp Leu Val Lys Ala
    610                 615                 620

```
(2) INFORMATION FOR SEQ ID NO:28:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

Ile Asp Trp His Val Ser Gly Gly Leu Ala Leu
1               5                   10

(2) INFORMATION FOR SEQ ID NO:29:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

Leu Glu Ala Gly Phe Ala Leu Val
1               5
```

BLUE COPPER OXIDASE MUTANTS WITH ENHANCED ACTIVITY

CROSS REFERENCE TO RELATED APPLICATIONS

This application is a divisional of Ser. No. 08/706,037 filed Aug. 30, 1996, now U.S. Pat. No. 5,770,419, which claims priority under 35 U.S.C. 119 of Ser. No. 60/003,142 filed Sep. 1, 1995, the contents of which are fully incorporated herein by reference.

BACKGROUND OF THE INVENTION

1. Field of the Invention

The present invention relates to mutant multi-copper oxidases. More specifically, the invention relates to oxidases which have been modified so as to exhibit altered pH activity profiles relative to the wild-type oxidase.

2. Description of the Related Art

There are currently a number of well-known blue copper oxidases which have various commercial/industrial applications. Two major classes of these enzymes are recognized: (1) the single copper proteins, which are single copper-containing, blue electron-transfer proteins such as plastocyanin, azurin, stellacyanin, amicyanin, auracyanin, cucumber basic blue, mavicyanin, rusticyanin, and urnecyanin; and (2) the multi-copper oxidases, which are multiple copper-containing, blue oxidoreductases such as laccase, bilirubin oxidase, phenoxazinone synthase, ascorbate oxidase, ceruloplasmin, and nitrite reductase. The blue color of these proteins arises from the so-called Type 1 (T1) copper site.

It is an object of the present invention to provide mutants of blue multi-copper oxidases which have improved properties.

BRIEF DESCRIPTION OF THE FIGURES

FIGS. 6a–6e show the nucleotide sequence and the deduced amino acid sequence of *Rhizoctonia solani* laccase isozyme 4 (rsl4) gene (SEQ ID NOS:24 and 25).

FIGS. 7a–7f show the nucleotide sequence and the deduced amino acid sequence of *Myceliophthora thermophila* laccase lcc-1 gene (SEQ ID NOS:26 and 27).

SUMMARY OF THE INVENTION

Figure 1A:
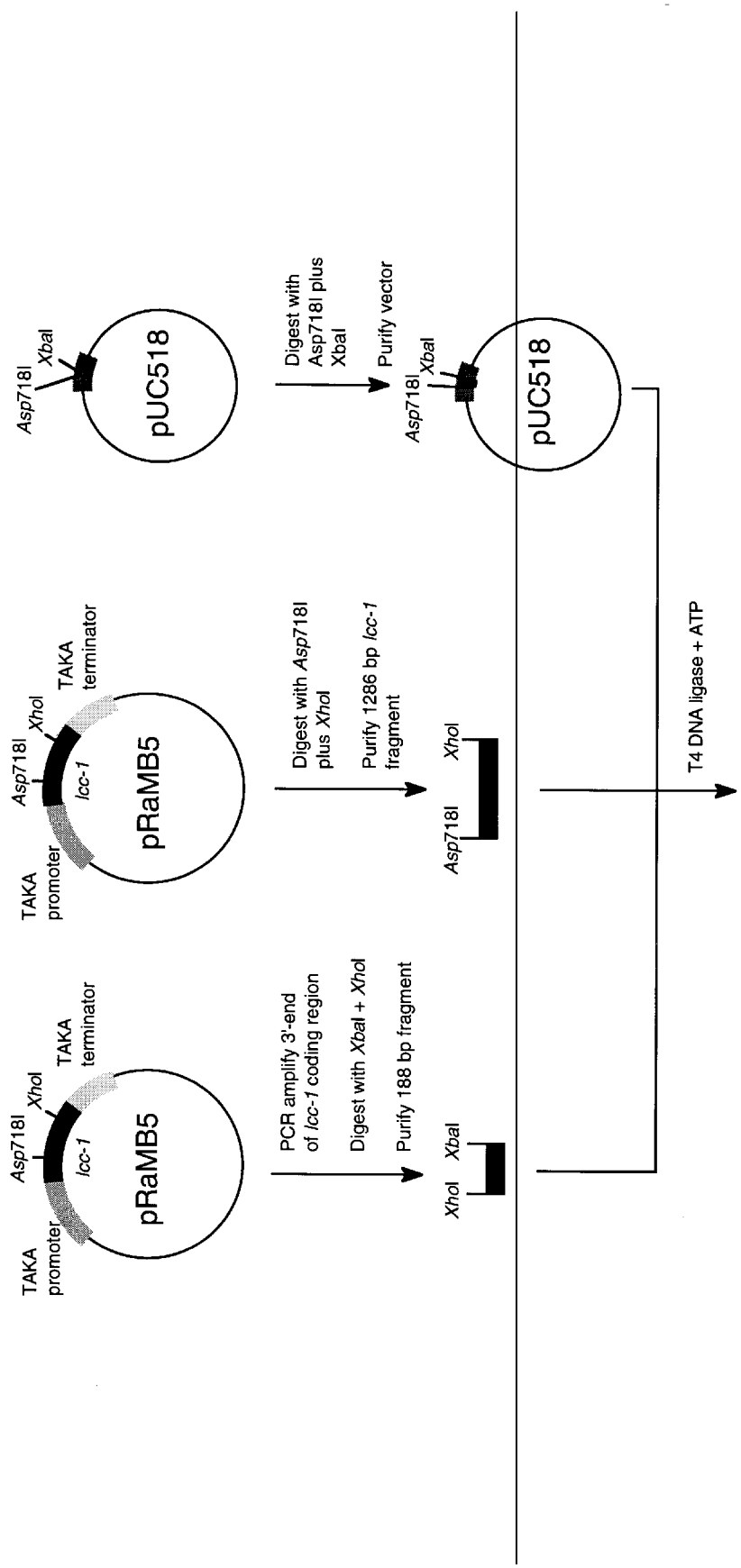
FIG. 1 shows the scheme for construction of intermediate plasmid pInt2.22 and oligonucleotide-directed mutagenesis of the *Myceliophthora thermophila* lcc-1 gene.
Figure 1B:
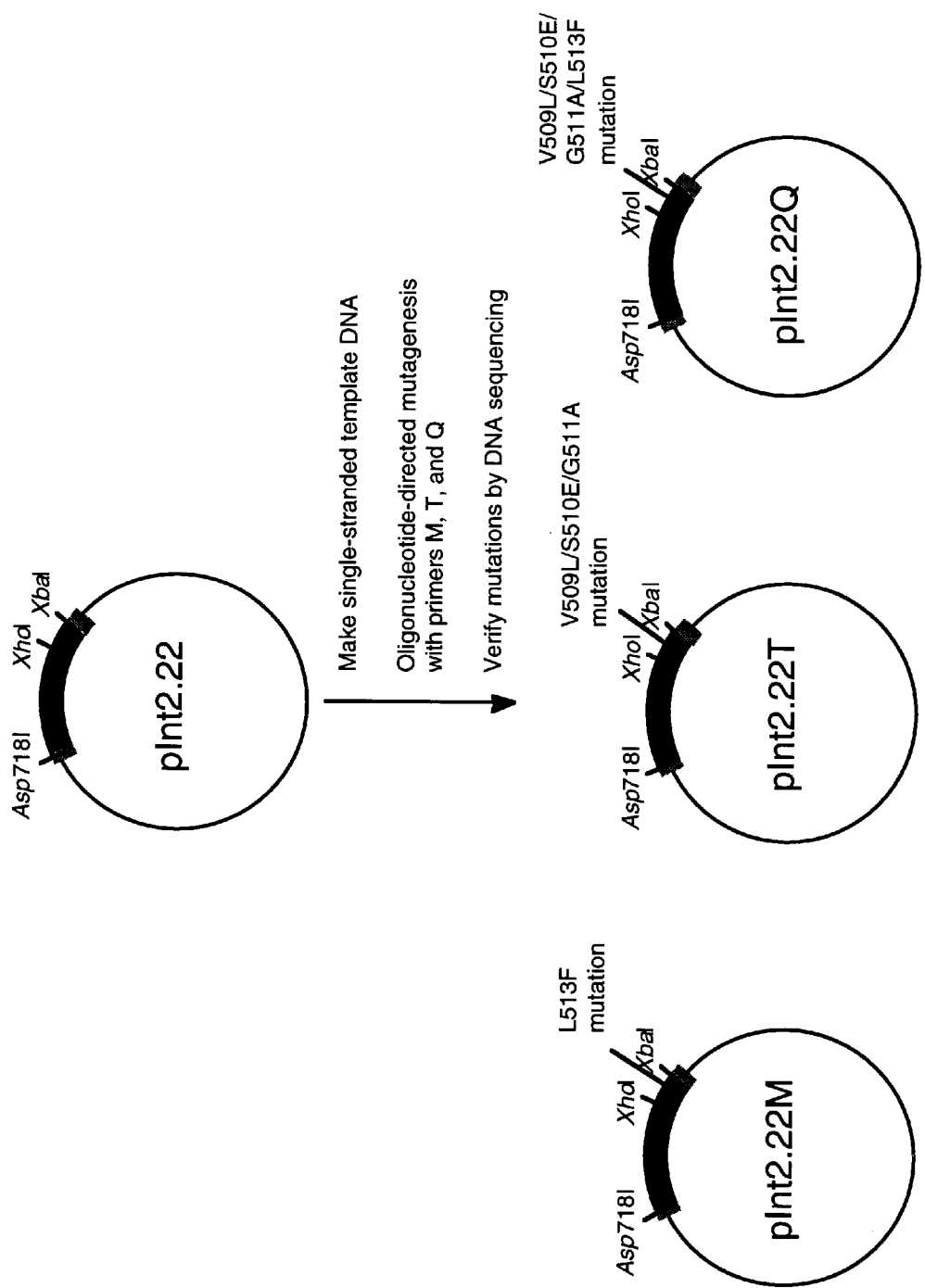

The present invention relates to mutants of a blue multi-copper oxidase, comprising a mutation selected from the group consisting of (a) a substitution of one or more amino acid residues with other amino acid residues, (b) an insertion of one or more amino acid residues and/or (c) a deletion of one or more amino acid residues, wherein the substitution, insertion or deletion is carried out at a position which is located no greater than 15 Å from a Type I (T1) copper site. The present invention also relates to nucleic acid constructs comprising a nucleic acid sequence encoding the mutants of the present invention, host cells comprising the construct of the present invention, and methods for producing mutants of the present invention.

DETAILED DESCRIPTION OF THE INVENTION

The present invention relates to mutants of a blue multi-copper oxidase, comprising (a) a substitution of one or more amino acid residues with other amino acid residues, (b) an insertion of one or more amino acid residues and/or (c) a deletion of one or more amino acid residues, wherein the substitution, insertion or deletion is carried out at a position which is located no greater than 20 Å from a Type I (T1) copper site. Preferably, each mutation is a substitution of one or more amino acid residues with other amino acid residues.

The Type 1 copper site consists of four ligands which bind to a copper ion, each of which is either an amino acid residue of the blue copper oxidase or a small molecule such as a water molecule. A ligand is defined herein an amino acid residue of a blue copper oxidase which binds to a copper ion. The Type 1 copper site of all known blue copper oxidases consists of the following ligands: two histidines (H), one cysteine (C), and, possibly, one additional methionine.

The ligand location for *Rhizoctonia solani* is: H 427, C 480, H 485 and possibly L 470 and for *Myceliophthora thermophilum* is H 431, C 503, H 508 and possibly L 513.

For purposes of the present invention, the distance from a Type I copper site is measured from the copper ion.

In a preferred embodiment, the mutant has a mutation at a position which is located no greater than 15 Å from a Type I copper site. In another preferred embodiment, the mutant has a mutation at a position which is located no greater than 12 Å from a Type I copper site. In another preferred embodiment, the mutant has a mutation at a position which is located no greater than 10 Å from a Type I copper site. In another preferred embodiment, the mutant has a mutation at a position which is located no greater than 8 Å from a Type I copper site. In another preferred embodiment, the mutant has a mutation at a position which is located no greater than 6 Å from a Type I copper site. In another preferred embodiment, the mutant has a mutation at a position which is located no greater than 4 Å from a Type I copper site. In another preferred embodiment, the mutant has a mutation at a position which is located no greater than 2.5 Å from a Type I copper site. In another preferred embodiment, the mutant has a mutation of an amino acid residue which is adjacent to a Type I copper site ligand. In another preferred embodiment, the mutant has a mutation of an amino acid residue which is a Type I copper site ligand.

The mutants of the present invention are mutants of a blue multi-copper oxidase. Preferably, the blue multi-copper oxidase is a bilirubin oxidase (Kokeida et al., 1993, *Journal of Biological Chemistry* 268: 18801–18809). In another preferred embodiment, the blue multi-copper oxidase is a phenoxazinone synthase (Freeman et al., 1993, *Biochemistry* 32: 4826–4830). In another preferred embodiment, the blue multi-copper oxidase is an ascorbate oxidase (Tauber et al., 1935, *Journal of Biological Chemistry* 110: 211). In another preferred embodiment, the blue multi-copper oxidase is a ceruloplasntin (Curzon and Young, 1972, *Biochimica Biophysica Acta* 268: 41). In another preferred embodiment, the blue multi-copper oxidase is a nitrite reductase (Godden et al., 1991, *Science* 253: 438–442). In another preferred embodiment, the blue multi-copper oxidase is a laccase. In a most preferred embodiment, the blue multi-copper oxidase is a fungal laccase, e.g., a Rhizoctonia laccase (preferably a *Rhizoctonia solani* laccase or RsL; WO 95/07988) or a Myceliophthora laccase (preferably a *Myceliophthora thermophilum* laccase or MtL described in U.S. application Ser. No. 08/253,781, which is incorporated herein by reference).

In another preferred embodiment, the oxidase is another Rhizoctonia laccase (as disclosed in U.S. Pat. No. 5,480,801, which is incorporated herein by reference), another Myceliophthora laccase (as disclosed in U.S. application Ser. No. 08/253,781, which is incorporated herein by reference), and laccases of Polyporus (as disclosed in U.S. application Ser. No. 08/441,147, which is incorporated herein by reference), *Trametes, Pyricularia, Coriolus, Scytalidium* (as disclosed in U.S. application Ser. No. 08/253,784, which is incorporated herein by reference), Rigidoporus and Phenllinus (Geiger et al., 1986, *Appl. Biochem. Biotech.*, 13: 97–110), Podospora (Moltitoris and Reinhammar, 1974, *Biochimica Biophysica Acta* 386: 493–502), Lentinus (Leatham and Stahmann, 1980, *Journal of General Microbiology* 125: 147–157), Neurospora (Germann et al., 1987, *Journal of Biological Chemistry* 263: 885–896), Aspergillus (Kurtz and Champe, 1982, *Journal of Bacteriology* 151: 1338–1345), Phlebia (Niku-Paavola et al., 1988, *Biochemical Journal* 254:877–884), Botrytis (Dubernet et al., 1976, *Phytochemistry* 16: 191–193,), Sclerotia (Chet and Huttermann, 1982, FEMS *Microbiological Letters* 14: 211–215), Curvularia (Banerjee and Vohra, 1991, *Folia Microbiol.* 36: 343–346), Fomes (Haars and Huttermann, 1983, *Arch. Microbiol.* 134: 309–313), Schizophyllum (De Vries et al., 1986, *Journal of General Microbiology* 132: 2817–2826), Cerrena (Bekker et al., 1990, *Biokhimia* 55: 2019–2024), Armillaria (Rehman and Thurston, 1992, *Journal of General Microbiology* 138: 1251–1257), Agaricus (Perry et al., 1993, *Journal of General Microbiology* 139: 1209–1218), Pleurotus (Von Hunolstein et al., 1986, *Journal of General Applied Microbiology* 32: 185–191), Acer pseudopaltanus (Lafayette et al., 1995, *Plant Physiology* (Rockville) 107: 667–668), and Rhus (Bertrand, 1895, *C. R. Acad. Sci. Paris* 121: 166).

The mutants of the present invention may have a different specific activity than the wild-type blue copper oxidases. For example, a negative charge, or more precisely, a relatively high electron density, in the T1 copper site region is important for activity.

Furthermore, the mutants of the present invention may have a different pH-activity profile than the wild-type blue copper oxidases, e.g., the mutants can have a higher or lower pH optimum by an alteration of the charge distribution (or dielectric anisotrophy) at the T1 copper site. In order to enhance the activity of the oxidase of interest in a more alkaline pH range, electron density and/or negative charge should be increased. Thus, in the mutants of the present invention, (a) a neutral amino acid residue is substituted with a negative amino acid residue or (b) a positive amino acid residue is substituted with a negative or neutral amino acid residue. In addition, neutral residues equipped with a functional group that bear a relatively high electron density and could act as general base, such as histidine, serine, threonine, tyrosine, cysteine, and methionine, may also be used to substitute other neutral residues possessing only simple aliphatic or aromatic side chains, such as leucine and phenylalanine. In order to enhance the activity of the oxidase of interest in a more acidic pH range, electron density and/or negative charge should be decreased. Thus, in this embodiment of the mutants of the present invention, (a) a neutral amino acid residue is substituted with a positive amino acid residue or (b) a negative amino acid residue is substituted with a positive or neutral amino acid residue.

The present invention also relates to mutants which can be expressed in higher yields. Such mutants include oxidases comprising a substitution of a phenylalanine with another amino acid residue. For example, substituting phenylalanine at a position corresponding to residue 513 of *Myceliophthora thermophila* laccase and position 470 in *Rhizoctonia solani* isozyme 4 laccase results in a low expression yield. Thus, the mutants of the present invention encompass substitutions of Phe at one of these positions with another amino acid residue. Preferably, the amino acid residue does not ligate to copper, i.e., the amino acid residue is not histidine, cysteine, methionine, glutamate, and aspartate. Preferably, phenylalanine is substituted by leucine. In a preferred embodiment, the yield of the mutant enzyme is increased at least two-fold, more preferably at least five-fold, over the yield observed with the corresponding wild-type enzyme when both are expressed in the same host and fermented under the same conditions.

In a preferred embodiment, the mutants of the present invention comprise a mutation in a region corresponding to: (a) the segment that contains one Cu-ligating His, e.g., 416VIELNITGGADHPI429 (SEQ ID NO:25) of *Rhizoctonia solani* laccase and 421ENDPGAPFTLPHPM433 (SEQ ID NO:27) of *Myceliophthora thermophila* laccase; (b) the segment that contains another ligating His and the ligating Cys, e.g., 474GPWFVHCHLDWHLEAGLALVF494 (SEQ ID NO:25) of *Rhizoctonia solani* laccase and 497GAWLF-HCHIAWHVSGGLGV515 (SEQ ID NO:27) of *Myceliophthora thermophila* laccase; (c) the segment corresponding to the sequence where Q353 and W362 of ascorbate oxidase reside, e.g., 356VSLNLAIGRSTVDGIL371 (SEQ ID NO:25) of *Rhizoctonia solani* laccase and 361VTLDTTGT-PLFVWKVN376 (SEQ ID NO:27) of *Myceliophthora thermophila* laccase; (d) the segment corresponding to the sequence where R285 of ascorbate oxidase resides, e.g., 303LDPTNVFAVL312 (SEQ ID NO:25) of *Rhizoctonia solani* laccase and 308AIFHYAGAPG317 (SEQ ID NO:27) of *Myceliopthora thermophila* laccase; (e) the segment corresponding to the sequence where W163 of ascorbate oxidase resides, e.g., 217INVKRGKRYR226 (SEQ ID NO:25) of *Rhizoctonia solani* laccase and 222GRRHRLR-LIN231 (SEQ ID NO:25) of *Myceliophthora thermophila* laccase; and (f) the segment corresponding to 465LEAGL472 (SEQ ID NO:25), more preferably 466LEAGL470(SEQ ID NO:25), of *Rhizoctonia solani* laccase. Those skilled in the art will readily recognize, by routine homology alignment, the corresponding regions in other blue copper oxidases. In a preferred embodiment, the mutants comprise a mutation in the segment corresponding to 416VIELNITGGADHPI429 (SEQ ID NO:25) of *Rhizoctonia solani* laccase and 421ENDPGAPFTLPHPM433 (SEQ ID NO:27) of *Myceliophthora thermophila* laccase.

In a preferred embodiment, the mutants comprise at least two amino acid residues, more preferably at least 3 amino acid residues. In another preferred embodiment, the mutants comprise five mutations, more preferably four mutations, even more preferably three mutations, even more preferably two mutations, and most preferably one mutation.

The mutants described herein are most efficiently prepared by site-directed mutagenesis of the DNA encoding the wild-type laccase of interest. Such techniques are well-known in the art, and are described in, for example, Sambrook et al., 1989, *Molecular Cloning, A Laboratory Manual*, Cold Spring Harbor Laboratory, Cold Spring Harbor, N.Y. The present invention also encompasses the nucleic acid encoding the mutant laccases, as well as vectors and host cells comprising same, for use in recombinant expression of the mutant enzyme.

The choice of host cells and expression vectors will to a large extent depend upon the enzyme of choice and its source. The mutant gene can be expressed, in active form, using an expression vector. A useful expression vector contains an element that permits stable integration of the vector into the host cell genome or autonomous replication of the vector in a host cell independent of the genome of the host cell, and preferably one or more phenotypic markers which permit easy selection of transformed host cells. The expression vector may also include control sequences encoding a promoter, ribosome binding site, translation initiation signal, and, optionally, a repressor gene, a selectable marker or various activator genes. To permit the secretion of the expressed protein, nucleotides encoding a signal sequence may be inserted prior to the coding sequence of the gene. For expression under the direction of control sequences, a laccase gene to be used according to the invention is operably linked to the control sequences in the proper reading frame. Promoter sequences that can be incorporated into plasmid vectors, and which can direct the transcription of the laccase gene, include, but are not limited to, the prokaryotic Δ-lactamase promoter (Villa-Kamaroff et al., 1978, *Proceedings of the National Academny of Sciences USA* 75: 3727–3731) and the tac promoter (DeBoer et al., 1983, *Proceedings of the National Academy of Sciences USA* 80: 21–25). Further references can also be found in "Useful proteins from recombinant bacteria" in 1980, *Scientific American* 242: 74–94; and in Sambrook et al., 1989, supra.

The expression vector carrying the nucleic acid construct of the invention may be any vector which may be conveniently subjected to recombinant DNA procedures. The vector may be an autonomously replicating vector, i.e., a vector which exists as an extrachromosomal entity, the replication of which is independent of chromosomal replication, e.g., a plasmid, or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the nucleic acid sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA construct of the invention, especially in a bacterial host, are the promoter of the lac operon of *E. coli*, the *Streptomyces coelicolor* agarase gene dagA promoters, the promoters of the *Bacillus licheniformis* alpha-amylase gene (amyL), the promoters of the *Bacillus stearothernophilus* maltogenic amylase gene (amyM), the promoters of the *Bacillus amyloliquefaciens* alpha-amylase (amyQ), or the promoters of the *Bacillus subtilis* xylA and xylB genes. In a yeast host, a useful promoter is the ENO-1 promoter. For transcription in a fungal host, examples of useful promoters are those derived from the gene encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase or *Aspergillus nidulans* acetamidase. Preferred are the TAKA-amylase and glaA promoters.

The expression vector of the invention may also comprise a suitable transcription terminator and, in eukaryotes, polyadenylation sequences operably connected to the DNA sequence encoding the laccase of the invention. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g., a gene the product of which complements a defect in the host cell, such as the dal genes from *Bacillus subtilis* or *Bacillus licheniformis*, or one which confers antibiotic resistance such as ampicillin, kanamycin, chloramphenicol or tetracycline resistance. Examples of Aspergillus selection markers include amdS, pyrG, argB, niaD, sC, and hygB a marker giving rise to hygromycin resistance. Preferred for use in an Aspergillus host cell are the amdS and pyrG markers of *Aspergillus nidulans* or *Aspergillus oryzae*. A frequently used mammalian marker is the dihydrofolate reductase (DHFR) gene. Furthermore, selection may be accomplished by co-transformation, e.g., as described in WO 91/17243.

It is generally preferred that expression gives rise to a product that is extracellular. The laccases of the present invention may thus comprise a preregion permitting secretion of the expressed protein into the culture medium. If desirable, this preregion may be native to the laccase of the invention or substituted with a different preregion or signal sequence, conveniently accomplished by substitution of the DNA sequences encoding the respective preregions. For example, the preregion may be derived from a glucoamylase or an amylase gene from an Aspergillus species, an amylase gene from a Bacillus species, a lipase or proteinase gene from *Rhizomucor miehei*, the gene for the alpha-factor from *Saccharomyces cerevisiae*, or the calf preprochymosin gene. Particularly preferred, when the host is a fungal cell, is the preregion for *Aspergillus oryzae* TAKA amylase, *Aspergillus niger* neutral amylase, the maltogenic amylase form Bacillus NCIB 11837, *Bacillus stearothernophilus* alpha-amylase, or *Bacillus licheniformis* subtilisin. An effective signal sequence is the *Aspergillus oryzae* TAKA amylase signal, the *Rhizomucor miehei* aspartic proteinase signal, and the *Rhizomucor miehei* lipase signal.

The procedures used to ligate the nucleic acid construct of the invention, the promoter, terminator and other elements, respectively, and to insert them into suitable vectors containing the information necessary for replication, are well known to persons skilled in the art (cf., for instance, Sambrook et al., 1989, supra).

The cell of the invention either comprising a nucleic acid construct or an expression vector of the invention as defined above is advantageously used as a host cell in the recombinant production of an enzyme of the invention. The cell may be transformed with the nucleic acid construct of the invention, conveniently by integrating the construct into the host chromosome. This integration is generally considered to be an advantage as the sequence is more likely to be stably maintained in the cell. Integration of the constructs into the host chromosome occurs by homologous or heterologous recombination. Alternatively, the cell may be transformed with an expression vector as described above in connection with the different types of host cells.

The host cell may be selected from prokaryotic cells, such as bacterial cells. Examples of suitable bacteria are gram positive bacteria such as *Bacillus sublilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gram negative bacteria such as *E. coli*. The transformation of the bacteria may, for instance, be effected by protoplast transformation or by using competent cells in a manner known per se.

The host cell is preferably a eukaryote, such as mammalian cells, insect cells, plant cells or preferably fungal cells, including yeast and filamentous fungi. For example, useful mammalian cells include CHO or COS cells. A yeast host cell may be selected from a species of Saccharomyces or Schizosaccharomyces, e.g., *Saccharomyces cerevisiae*. Useful filamentous fungi may be selected from a species of Aspergillus, e.g., *Aspergillus oryzae* or *Aspergillus niger*. Alternatively, a strain of a Fusarium species, e.g., *Fusarium oxysporum*, or *Fusarium graminearum*, can be used as a host cell. Fungal cells may be transformed by a process involving protoplast formation and transformation of the protoplasts followed by regeneration of the cell wall in a manner known per se. A suitable procedure for transformation of Aspergillus host cells is described in EP 238 023. A suitable method of transforming Fusariun species is described by Malardier et al., 1989, *Gene* 78:147–156 or in copending U.S. application Ser. No. 08/269,449.

The present invention thus also provides a method of producing a recombinant protein of the invention, which method comprises cultivating a host cell as described above under conditions conducive to the production of the enzyme and recovering the enzyme from the cells and/or culture medium. The medium used to cultivate the cells may be any conventional medium suitable for growing the host cell in question and obtaining expression of the laccase of the invention. Suitable media are available from commercial suppliers or may be prepared according to published formulae (e.g., in catalogues of the American Type Culture Collection).

The resulting enzyme may be recovered from the medium by conventional procedures including separating the cells from the medium by centrifugation or filtration, precipitating the proteinaceous components of the supernatant or filtrate by means of a salt, e.g., ammonium sulphate, followed by purification by a variety of chromatographic procedures, e.g., ion exchange chromatography, gel filtration chromatography, affinity chromatography, or the like. Preferably, the isolated protein is about 90% pure as determined by SDS-PAGE, purity being most important in food, juice or detergent applications.

In a particularly preferred embodiment, the expression of the enzyme is achieved in a fungal host cell, such as Aspergillus. As described in detail in the following examples, the laccase gene is ligated into a plasmid containing the *Aspergillus oryzae* TAKA alpha-amylase promoter, and the *Aspergillus nidulans* amdS selectable marker. Alternatively, the amdS may be on a separate plasmid and used in co-transformation. The plasmid (or plasmids) is used to transform an Aspergillus species host cell, such as *Aspergillus oryzae* or *Aspergillus niger* in accordance with methods described in Yelton et al., 1984, *Proceedings of the National Academy of Sciences USA* 81: 1470–1474.

The modified oxidases, particularly laccases of the present invention can be used in a number of industrial methods. These processes include polymerization of lignin, both Kraft and lignosulfates, in solution, in order to produce a lignin with a higher molecular weight Such methods are described in, for example, Jin et al., 1991, *Holzorschung* 45: 467–468; U.S. Pat. No. 4,432,921; EP 0 275 544; PCT/DK93/00217, 1992.

The oxidases of the present invention can also be used for in situ depolymerization of lignin in Kraft pulp, thereby producing a pulp with lower lignin content. This use of these enzymes is an improvement over the current use of chlorine for depolymerization of lignin, which leads to the production of chlorinated aromatic compounds, which are an environmentally undesirable by-product of paper mills. Such uses are described in, for example, *Current Opinion in Biotechnology* 3: 261–266, 1992; *Journal of Biotechnology* 25: 333–339, 1992; Hiroi et al., 1976, *Svensk Papperstidning* 5: 162–166.

Oxidation of dyes or dye precursors and other chromophoric compounds leads to decolorization of the compounds. Laccase can be used for this purpose, which can be particularly advantageous in a situation in which a dye transfer between fabrics is undesirable, e.g., in the textile industry and in the detergent industry. Methods for dye transfer inhibition and dye oxidation can be found in WO 92/01406, WO 92/18683, EP 0495836 and Calvo, 1991, *Mededelingen van de Faculteit Landbouw-wetenschappen/ Rijiksuniversitet Gent*. 56: 1565–1567; Tsujino et al., 1991, *Journal of the Chemical Society* 42: 273–282; methods for the use of oxidation of dye and dye precursors in hair coloring are found in U.S. application Ser. Nos. 08/441,146 and 441,147, the contents of which are incorporated herein by reference.

The present laccase can also be used for the polymerization of phenolic or aniline compounds present in liquids. An example of such utility is the treatment of juices, such as apple juice, so that the laccase will accelerate a precipitation of the phenolic compounds present in the juice, thereby producing a more stable juice. Such applications have been described in Stutz, 1993, *Fruit Processing* 7/93, 248–252; Maier et al., 1990, *Dt. Lebensmittel-rindschau* 86: 137–142; Dietrich et al., 1990, *Fluss. Obst* 57: 67–73.

The present invention is further explained in the following non-limiting examples.

EXAMPLES

Materials and Methods

Chemicals used as buffers and substrates are commercial products of at least reagent grade.

The protocols for molecular biology experiments (including restriction digests, DNA ligations, gel electrophoresis, and DNA preparations) are adapted from either the instructions of the manufacturer or standard procedures (Sambrook et al., 1989, supra). All oligonucleotides are synthesized by an Applied Biosystems 294 DNA/RNA Synthesizer. Nucleotide sequences are determined by an Applied Biosystems automatic DNA Sequencer, Model 373A, version 1.2.0.

Example 1

Site-directed Mutagenesis of *Myceliophthora thermophila* laccase

The construction of a *Myceliophthora thermophila* laccase expression vector, pRaMB17, and several derivatives, pRaMB17M, pBANe22T, and pRaMB17Q, which direct expression of the *Myceliophthora thermophila* wild-type laccase and laccase variants, is shown FIGS. 1–4. The primers used in the constructions are summarrzed in Table 1.

The resulting phage vector, mp18–5' link, is then digested with SalI and BsaI (both sites in the synthetic linker region) and ligated with a 1.1 kb SalI-BsaI fragment from pTAKA-17 comprising the TAKA promoter region to generate the recombinant phage mp18–5'. Plasmid pUC18 (Yanisch-

TABLE 1

Primers

| Primer | Sequence |
| --- | --- |
| 1 | (forward) 5' dGTCGTCTACCTCGAGCGCGCC 3' (SEQ ID NO:1) |
| 2 | (reverse) 5' dGTCATCTAGACGCTCACGCCTTGACCAGCCA 3' (SEQ ID NO:2) |
| 3 | 5' dGTAGACGACGCCGAAGCCGCCCGAGAC 3' (SEQ ID NO:3) |
| 4 | 5' dGACGACGCCCAGGCCAGCCTCGAGGTGCCAGGCGATGTG 3' (SEQ ID NO:4) |
| 5 | 5' dGAGGTAGACGACGCCGAAGCCAGCCTCGAGGTGCCAGGCGATGTG 3' (SEQ ID NO:5) |
| 6 | 5' CGGTACCGTCTAGAGTCGCGATGCATC 3' (SEQ ID NO:6) |
| 7 | 3' CCGGGCCATGGCAGATCTCAGCGCTACGTAGGATC 5' (SEQ ID NO:7) |
| 8 | 5' ATGATGAAGTCCTTCATCAGCGCCGCGACGCTTTTGGTGGG 3' (SEQ ID NO:8) |
| 9 | 3' TACTACTTCAGGAAGTAGTCGCGGCGCTGCGAAAACCAC 5' (SEQ ID NO:9) |
| 10 | (forward) 5' dGGGTCTAGAGGTGACTGACACCTGGCGGT 3' (SEQ ID NO:10) |
| 11 | (reverse) 5' dTGACCCGGGAACTGGCCCCGACATTCCAGC 3' (SEQ ID NO:11) |
| 12 | 5' gggatttaaatATGAAGTCCTTCATCAGCGCC-3' (SEQ ID NO:12) |
| 13 | 5' gggttaattaaTtACGCCTTGACCAGCCACTCGCC-3' (SEQ ID NO:13) |
| 14 | 5' ATACACAACTGGATGATGAAGTCCTTCATCAGCG 3' (SEQ ID NO:14) |

Specifically, a small DNA fragment containing the 3'-terminus of the lcc-1 coding region (including stop codon) is generated by PCR using pRaMB5 (U.S. application Ser. No. 08/441,146, which is incorporated herein by reference) as a template for Pfu polymerase with primers 1 and 2 listed in Table 1. The 188 bp PCR product is digested with XbaI plus XhoI and purified by agarose gel electrophoresis. The purified fragment is then mixed in a three-part ligation reaction with an Asp718I-XhoI segment (1286 bp) of the lcc-1 gene from pRaMB5, and pUC518 (a derivative of pUC118; Vieira and Messing, 1987, *Methods in Enzymology* 153: 3-4), containing additional restriction sites for BglII, ClaI, XhoI and NsiI in the polylinker, which has been cleaved with Asp718I-XbaI. The resulting plasmid, pInt2.22, which contains approximately 1.5 kb of the lcc-1 coding region, is extended from an internal Asp718I site through the stop codon which is followed immediately by a XbaI site. Single-stranded pInt2.22 DNA template is prepared (Vieira and Messing, 1987, supra) and used as a template for oligonucleotide-directed mutagenesis (Adelman et al., 1983, DNA 2: 183–193) with primer 3 for L513F mutation, primer 4 for V509L/S510E/G511A mutation, and primer 5 for V509/S510E/G511A/L513F mutation to derive the precursor plasmids for pRaMB17, pRaMB17M, pBANe22T and pRaMB17Q.

Mutants are identified by hybridization with radiolabeled oligonucleotide primers 3, 4, and 5, and each mutation is verified by DNA sequence analysis.

Figure 2:
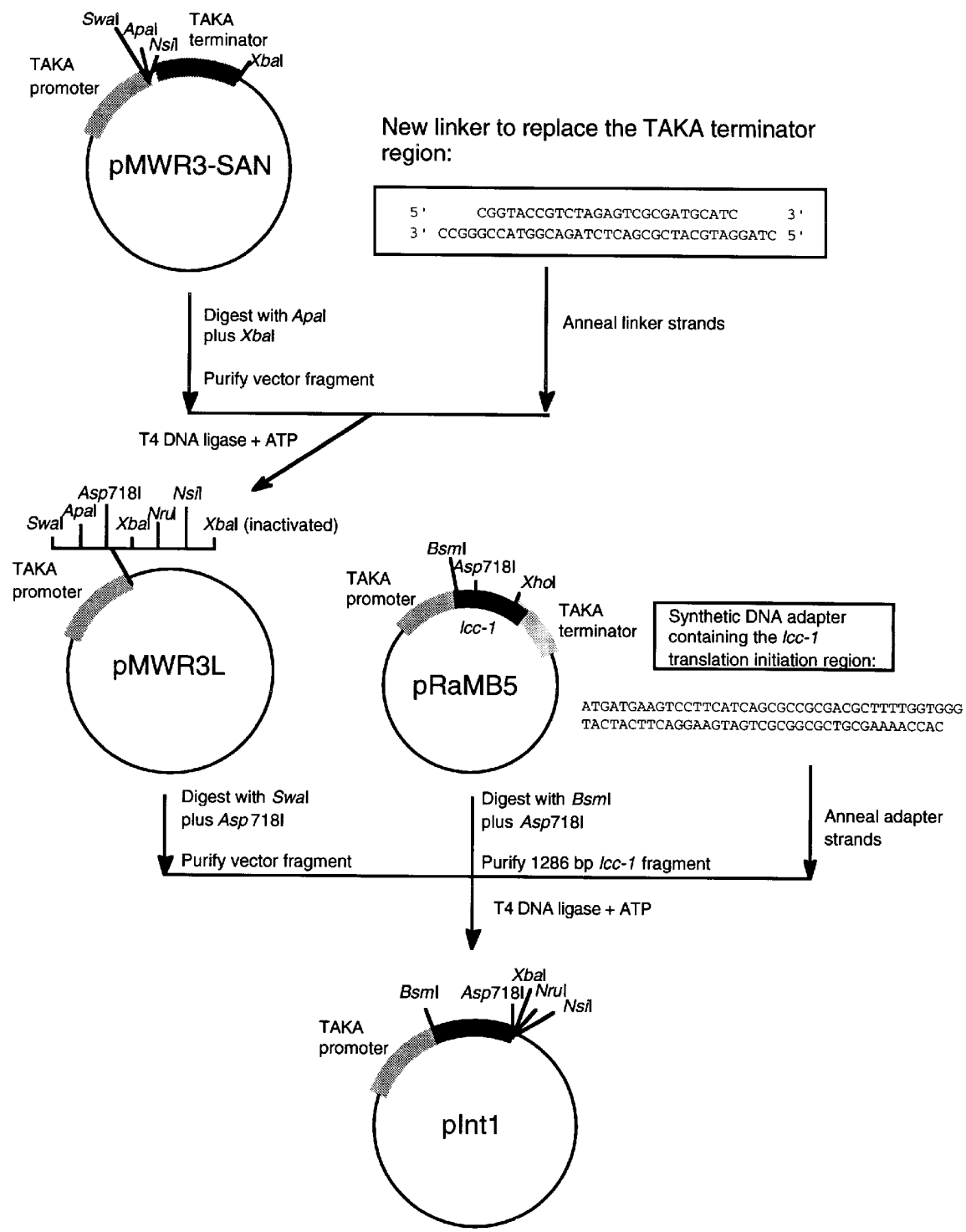
FIG. 2 shows the construction of the intermediate pInt1 which contains the *Aspergillus oryzae* TAKA amylase promoter and 5'-portion of the *Myceliophthora thermophila* lcc-1 coding region.
Figure 3:
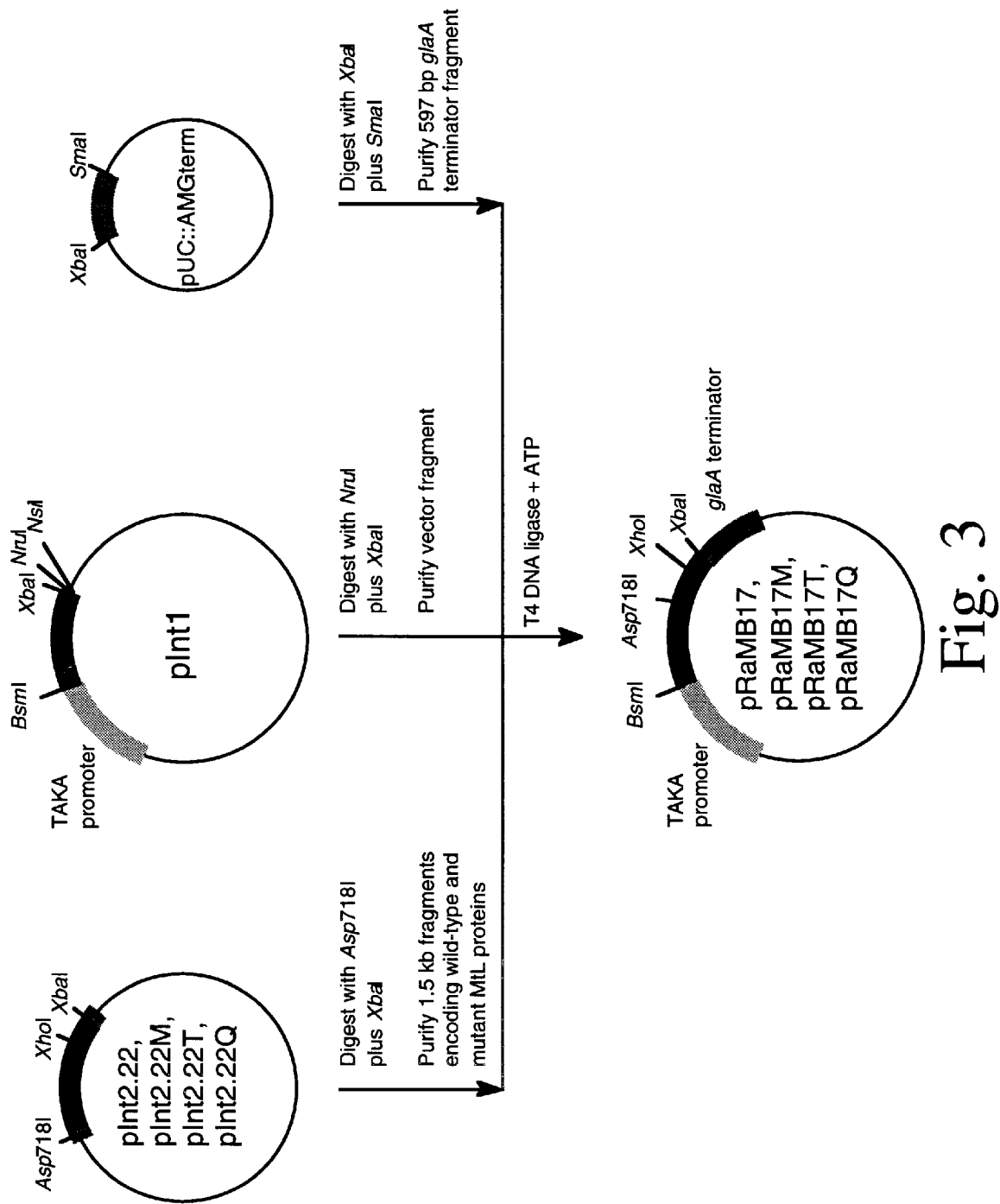
FIG. 3 shows the final step in construction of pRaMB17 and its derivatives, pRaMB17M and pRaMB17Q, which direct expression of wild-type and mutant forms of *Myceliophthora thernophila* laccase (MtL).

The next step in the construction of pRaMB17 and its derivatives is partially shown in FIG. 2. The starting plasmid, pMWR3-SAN, is prepared by cleaving bacteriophage vector M13mp18 (Yanisch-Perron et al., 1985, *Gene* 33: 103–119) with HindIII and EcoRI, and purifying the large vector fragment by agarose gel electrophoresis. This fragment is ligated with a synthetic DNA linker having the following sequence:

Perron et al., 1985, supra) is digested with HindIII plus EcoRI and the 2.6 kb vector fragment is purified by agarose gel electrophoresis. The isolated fragment is ligated with a synthetic linker with the following sequence:

5'         AATTGTTTAAACTCTAGAGAAT-
    TCAAGCTTGTCGACGTTTAAAC-
    CAAATTTGAGATCTCTTAAGTTCGAA-
    CAGCTGCAAATTTGTCGA 3' (SEQ ID NO:16)

The resulting plasmid, pUC18:: TAKA-link, is digested with SalI plus EcoRI and the vector fragment is isolated by agarose gel electrophoresis. pTAKA-17 is used as a template for PCR amplification of a 0.7 kb TAKA-amylase terminator fragment. For this purpose, the following primers are used:

forward primer: 5' dATGCATAGGGTGGAGAGTATAT-
    GATGG 3' (SEQ ID NO:17)

reverse primer: 5' dCTGAATTCCGTTTCGTTTAC 3' (SEQ ID NO:18)

The 0.7 kb product of this PCR reaction is digested with NsiI plus EcoRI and mixed in a three-part ligation with SalI and EcoRI cleaved pUC18:: TAKA-link and the 1.1 kb SalI-NsiI TAKA promoter fragment from mp18–5' to produce pMWR1.

Plasmid pMWRI is modified to generate pMWR3. First, a new TAKA-amylase promoter segment is generated by PCR using pTAKA-17 as a template with the following synthetic primers:

forward primer: 5' dTCCTGCAGAATGCAATT-
    TAAACTC 3' (SEQ ID NO:19)

reverse primer: 5' dCTATGCATATTTAAATGCCTTCT-
    GTGGGGTTTATTG 3' (SEQ ID NO:20)

The 0.2 kb PCR product is digested with NsiI plus PstI and ligated with the large vector fragment of pMWR1 which has been cleaved with NsiI and PstI. The resulting plasmid, pMWR3, is then modified by inserting a small linker, AATTGGGCCCATGCA (SEQ ID NO:21), which contains

```
5'AATTCGTCGACGGYCTCTATTTCTGTACGGCCTTCAGGTGGCCGCACCGGCCAT (SEQ ID NO:15)
GCATAGCAGCTGCCAGAGATAAAGACATGCCGGAAGTCCACCGGCGTGGCCGGT
ACGTATTCGA 3'
``` an ApaI site between the SwaI and NsiI sites, creating pMWR3-SAN. A derivative of pMWR3-SAN is then constructed by replacing the ApaI-XbaI TAKA-amylase terminator fragment with a small linker (primers 6 and 7 shown in Table 1). This linker introduces Asp718I, XbaI, and NruI cloning sites and inactivates the XbaI site of pMWR3-SAN yielding pMWR3L.

pMWR3L is digested with SwaI and Asp718I and mixed in a three-part ligation with a 853 bp BsmI-Asp718I fragment comprising the 5'-end of the lcc-1 coding region and synthetic DNA adapter containing the translation initiation region (primers 8 and 9 shown in Table 1) to yield plasmid pInt1.

A 597 bp DNA segment comprising the *Aspergillus niger* glaA terminator region is then isolated by PCR using pHD414 (EP 238 023) as a template with primers 10 and 11 shown in Table 1, which introduce XbaI and SmaI sites at the 5' and 3'-ends of the terminator, respectively. The amplified DNA fragment is subsequently cleaved with XbaI plus SmaI and subcloned into pUC118 to generate plasmid pUC::AMGterm.

Finally, the 1.5 kb fragments containing the wild-type and mutant lcc-1 gene sequences are excised by digestion with Asp718I and XbaI and purified by agarose gel electrophoresis. Each of these fragments is mixed in a three part ligation (FIG. 3) with Asp718 and NruI digested pInt1 plus the 597 bp XbaI-SmaI glaA terminator fragment from pUC::AMGterm to produce pRaMB17, pRaMB17M, pRaMB17T and pRaMB17Q.

Figure 4:
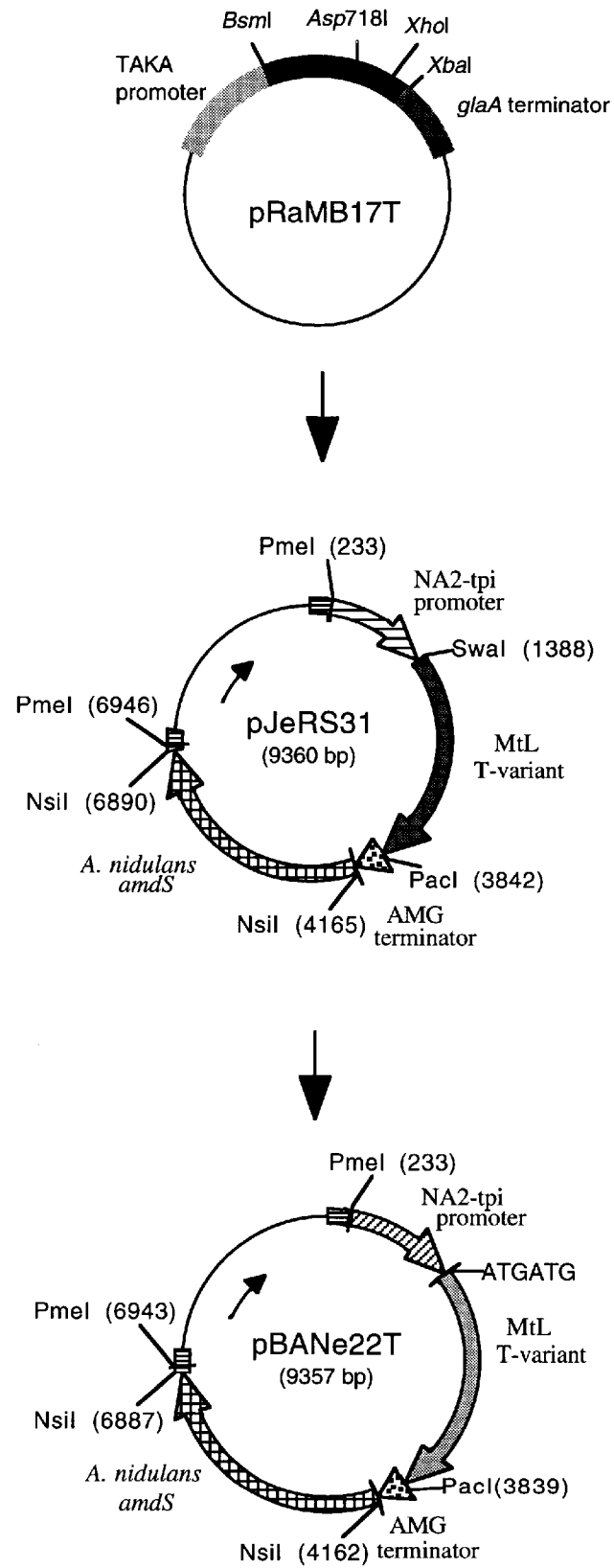
FIG. 4 shows the construction of pBANe22T which directs expression of a mutant form of *Myceliophthora thermophila* laccase.
Figure 5A:
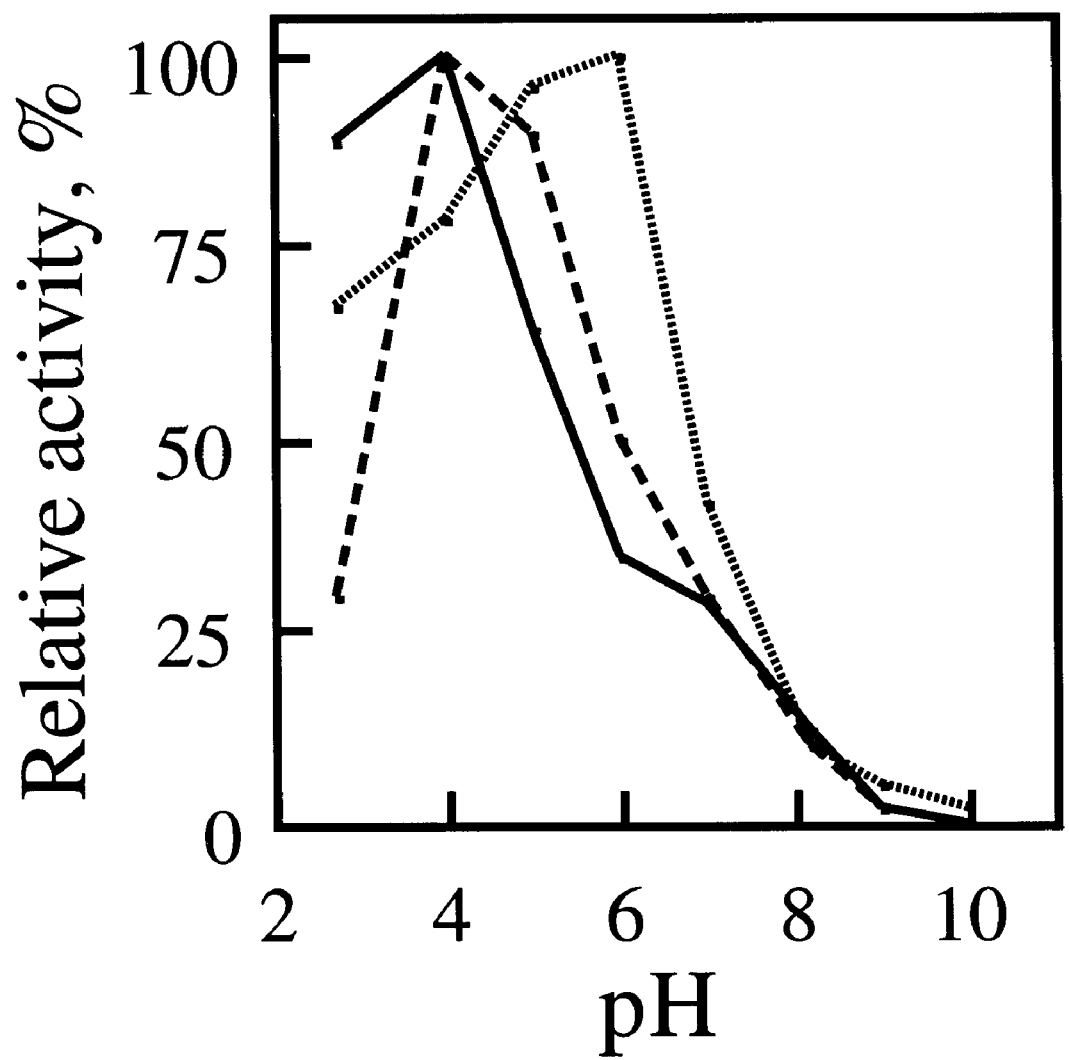
FIG. 5 shows the pH activity profiles of the wild-type (wt) and mutant *Rhizoctonia solani* laccases (RsLs) and *Myceliophthora thermophila* laccases (MtLs): wt (———); mutant M (-----); mutant T (.....); (A), RsL with 2,2'-azinobis(3-ethylbenzthiazoline-6-sulfonic acid) (ABTS); (B), RsLs with syringaldazine (SGZ); (C), MtLs with ABTS; (D), MTLS with SGZ.
Figure 5B:
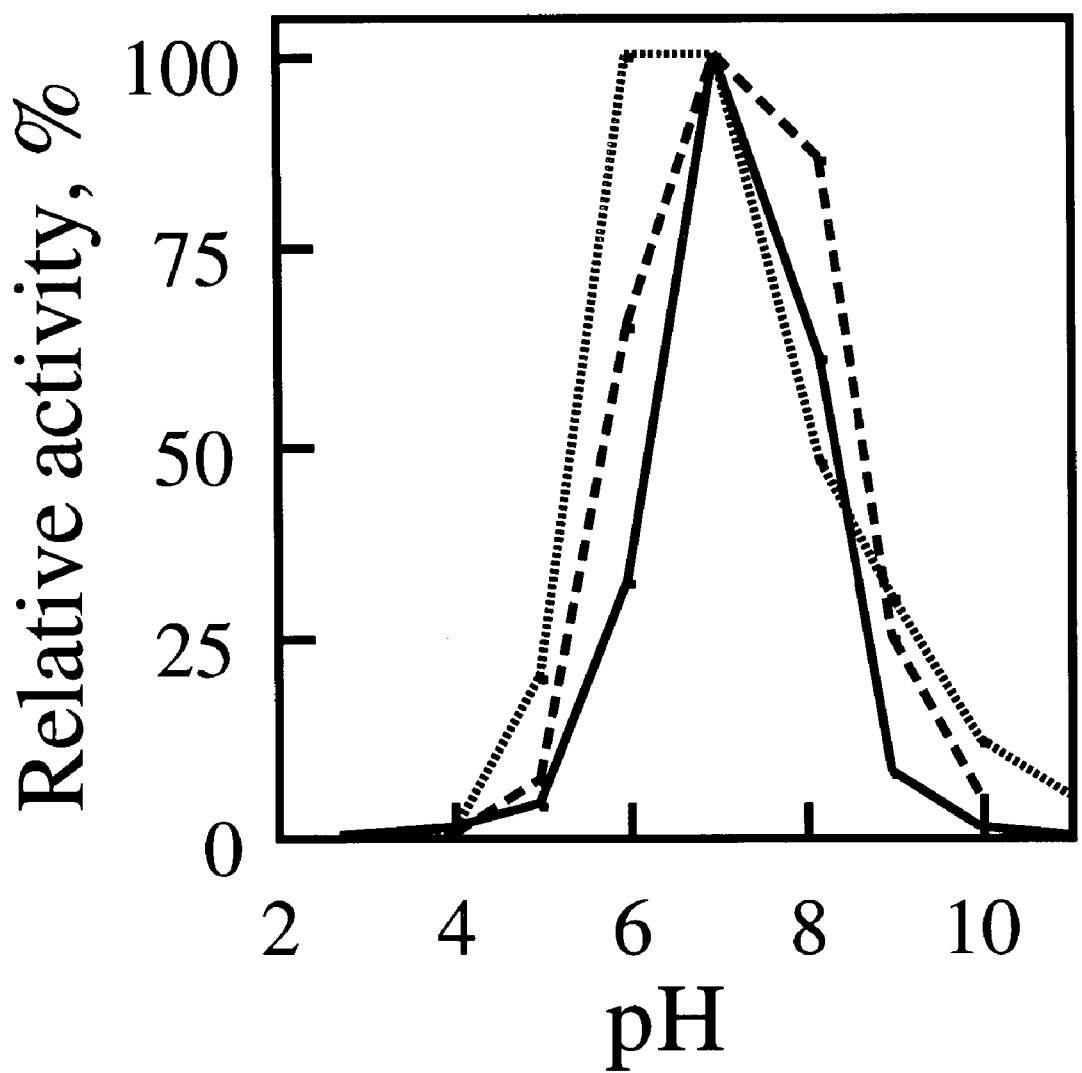
Figure 5C:
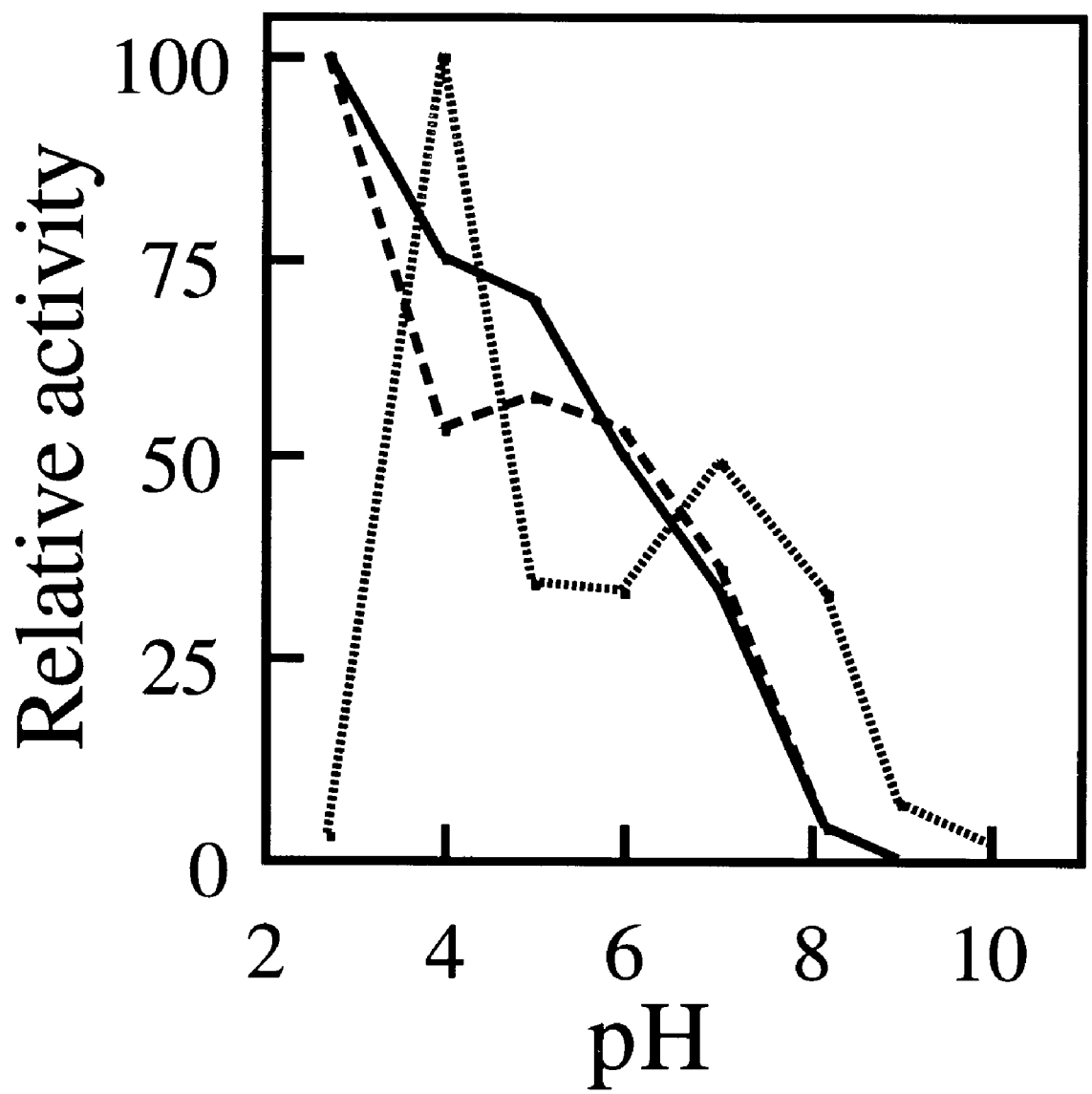
Figure 5D:
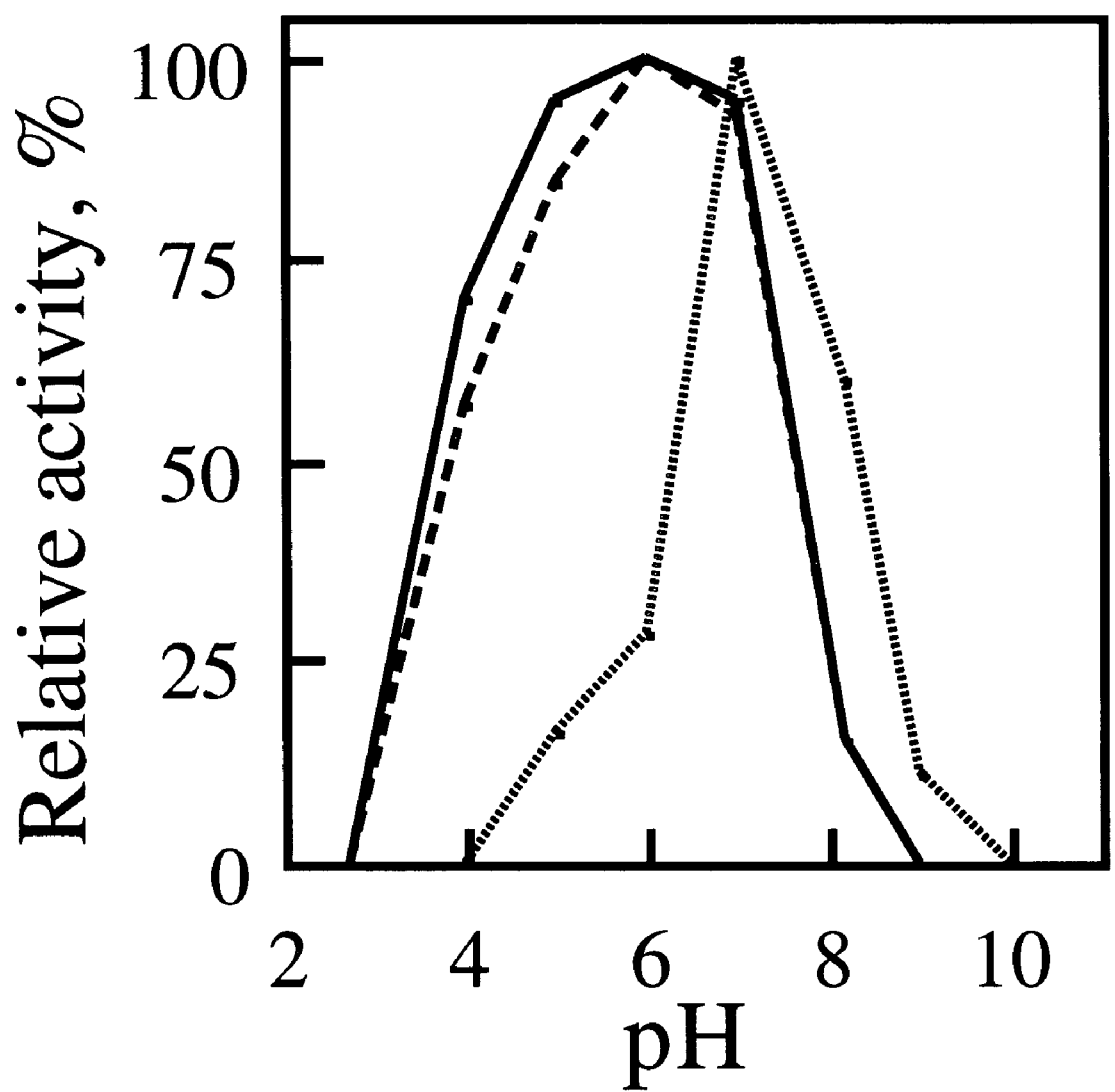

DNA primers 12 and 13 (uppercase letters represent sequences in the laccase gene) are used in a PCR reaction to amplify the mutant laccase gene from plasmid pRaMB17T (FIG. 4). The PCR is performed in a 50 ml reaction containing 120 ng of plasmid pRaMB17T, 0.05 mM each of dATP, dTTP, dGTP, dCTP, 100 pmol each of primers 12 and 13, 1X PwoI Buffer (Boehringer Mannheim, Indianapolis, Ind.), 5% (v/v) DMSO, and 2.5 units PwoI (Boeringer Mannheim, Indianapolis, Ind.). The PCR conditions are 95° C. for 3 minutes, 30 cycles each at 95° C. for 1 minute, 60° C. for 1 minute, and 72° C. for 1.5 minutes, an then 72° C. for 5 minutes. The PCR reaction mixture is run on a agarose gel and the 2.4 kb DNA laccase band is excised. The DNA is purified by solubilization of the agarose with 3 volumes Qia-ex solubilization buffer (Qiagen, Los Angeles, Calif.) followed by a Qiaquick PCR spin column according to the manufacturer's directions (Qiagen, Los Angeles, Calif.). The DNA is recovered in 50 ml of 1 mM EDTA-10 mM Tris pH 8 buffer. A 20 μl aliquot of the DNA is cut in a final volume of 25 μl containing 1X restriction enzyme buffers and restriction enzymes PacI and SwaI as suggested by the manufacturer. The reaction mixture is then heated at 80° C. for 10 minutes. One ml of the PacI/SwaI cut laccase gene is ligated into PacI/SwaI cut plasmid pBANe6. The ligation mixture is used to transform *E. coli* strain DH5α. The plasmid containing pBANe6 and the mutant laccase sequences is designated pJeRS31. pleRS31 is subjected to site-directed mutagenesis using primer 14 to remove the SwaI site and add a second ATG using the MORPH Site-Specific Plasmid DNA Mutagenesis Kit according to the manufacturer's instructions (5 Prime 3 Prime, Inc., Boulder, Colo.) to produce pBANe22T.

A summary of the plasmids is provided in Table 2.

TABLE 2

| pRaMB17 and its derivatives | |
|---|---|
| Vector | MtL protein encoded |
| pRaMB17 | Wild-type MtL |
| pRaMB17M | MtL with the L513F mutation |
| pBANe22T | MtL with the triple substitution V509L/S510E/G511A |
| pRaMB17Q | MtL with the quadruple substitution V509L/S510E/G511A/L513F |

Example 2

Transformation of *Aspergillus oryzae* with Modified *Myceliophthora thermophila* laccase Genes Methods for co-transformation of *Aspergillus oryzae* are described by Christensen et al., 1988, *Bio/Technology* 6: 1419–1422. For introduction of each of the *Myceliophthora thermophila* laccase expression vectors pRamB17, pRamB17M, pBANe22T, and pRamB17Q into *Aspergillus oryzae* HowB711, equal amounts (approximately 5 μg each) of the laccase expression vector and pToC90 (WO 91/17243) are added to approximately 106 protoplasts in suspension while pBANe22T is added alone. Transformants are selected on Cove medium (Cove, 1966, *Biochimica Biophysica Acta* 113: 51–56) containing 1 M sucrose, 10 mM acetamide as the sole nitrogen source, and 20 mM CsCl to inhibit background growth. The transformants selected in this way are subsequently screened for the ability to produce laccase on Cove medium containing 1–3 mM ABTS. Cells which secrete active laccase oxidize the ABTS, producing a green halo surrounding the colony. Transformants which produce detectable laccase activity on ABTS plates are purified twice through conidiospores.

Example 3

Expression of Modified *Myceliophthora thermophila* laccases

The transformants described in Example 2 are grown in shake flask cultures containing 25 ml of ASPO4 medium (pRaMB17, pRaMB17M, pRaMB17Q) or MY51 medium (pBANe22T) for 4 to 5 days at 37° C. ASPO4 medium is comprised of 1 g of $CaCl_2\text{-}2H_2O$, 2 g of yeast extract, 1 g of $MgSO_4$, 2 g of citric acid, 5 g of $KH_2PO_4$, 1 g of urea, 2 g of $(NH_4)_2SO_4$, 20 g of maltodextin, and 0.5 ml of trace metals solution per liter. MY51 medium is comprised of 50 g of maltodextrin, 2 g $MgSO_4\text{-}7H_2O$, 10 g of $KH_2PO_4$, 2 g of citric acid 10 g of yeast extract, 2 g of urea, 1 g of urea, 2 g of $(NH_4)_2SO_4$, and 0.5 ml of trace metals solution. The trace metals solution is comprised of 14.3 g of $ZnSO_4\text{-}7H_2O$, 2.5 g of $CuSO_4\text{-}5H_2O$, 0.5 g of $NiCl_2\text{-}6H_2O$, 13.8 g of $FeSO_4\text{-}7H_2O$, 8.5 g of $MgSO_4\text{-}H_2O$, and 3.0 g of citric acid per liter of RO water. Culture supernatants are assayed for laccase activity using either ABTS or syringaldazine as a substrate as described below.

Syringaldazine (SGZ) oxidation is determined in MES pH 5.3 buffer or Britten-Robinson buffer, pH 2.7 to 11.0, with 10% ethanol (coming from SGZ stock solution) by monitoring the absorbance change at 530 nm with an extinction coefficient of 65 $mM^{-1}cm^{-1}$ (Bauer and Rupe, 1971, *Analytical Chemistry* 43: 421–425) at 20° C. Laccase activity using SGZ as a substrate is assayed by mixing 800 μl of assay buffer (40 μM $CuSO_4$-25 mM sodium acetate pH 5.5) with 20 μl of culture supernatant and 60 μl of 0.28 mM syringaldazine in 50% ethanol. The absorbance at 530 nm is measured over time in a UV-VIS spectrophotometer. One laccase unit (LACU) is defined as the amount of enzyme which oxidizes one lmole of substrate per minute at 30° C.

ABTS oxidation is determined at pH 5 in a 96-well plate at 20° C. by monitoring the absorbance change at 405 nm with an extinction coefficient of 35 $mM^{-1}cm^{-1}$ (Childs and Bardsley, 1975, *Biochemical Journal* 145: 93–103). Laccase activity using ABTS as a substrate is measured by mixing 20 µl of culture supernatant with 200 µl of substrate solution containing 0.275 mg of ABTS per ml of 100 mM sodium acetate pH 5.0.

Shake flask cultures producing high levels of extracellular laccase activity are further evaluated by fermentation. A 1 ml aliquot of a spore suspension (approximately 109 spores) of an *Aspergillus oryzae* transformant expressing the laccase variant of interest is added aseptically to each of several 500 ml shake flasks containing 100 ml of medium comprised of 50 g of Nutriose 725, 2 g of $MgSO_4$-$7H_2O$, 10 g of $KH_2PO_4$, 2 g of $K_2SO_4$, 0.5 g of $CaCl_2$-$2H_2O$, 2 g of citric acid, 10 g of yeast extract, 0.5 ml of trace metals (as described above), and 2 g of urea per liter of tap water (adjusted to pH 6.0 before autoclaving) and incubated at 34° C. on a rotary shaker at 200 rpm for about 18 hours. Samples of the shake flask broths are then transferred to a laboratory fermentor containing medium, supplemented with 2 mM $CuSO_4$-$5H_2O$, comprised of 30 g of Nutriose, 5 g of yeast extract, 2 g of $(NH_4)_2HPO_4$, 2 g of $MgSO_4$-$7H_2O$, 4 g of citric acid, 3 g of $K_2SO_4$, 2 g of $CaCl_2$-$H_2O$, and 0.5 of trace metals solution (as described above) per liter and fed during the course of the fermentation with a medium comprised of 270 g of Nutriose, 30 g of urea, and 15 g of yeast extract per liter. The fermentaion is allowed to proceed at 31° C., pH 7, 600–700 rpm for 7 days.

Laccase yields for the "M" (L513F) and "T" (V509L/S510E/G511A) mutants from these fermentations are estimated to be 25% and 40%, respectively, of the wild-type yield. In contrast, the expression yield of mutant "Q" (V509L/S510 E/G511A/L513F) is so low that there is insufficient laccase for purification.

Example 4
Purification of Modified *Myceliophthora thermophila* laccases

The wild-type, "M", and "T" fermentation broths from Example 3 are cheese-cloth filtered (pH 7.6, 16 mS), filtered through Whatman #2 filter paper, concentrated on a Spiral Concentrator (Amicon) with a S1Y100 membrane (100 kDa MW-CO), and diluted to 0.75 mS with glass distilled water. The washed concentrated broths are loaded onto a Q-Sepharose XK26 (Pharmacia, Uppsala, Sweden) column (120 ml), pre-equilibrated with 10 mM Tris, pH 7.5, 0.7 mS (Buffer A), and active fractions are eluted during the linear gradient with Buffer B (Buffer A plus 2 M NaCl). The active fractions are pooled, adjusted to 1 mS in ionic strength, and subjected to a Mono-Q (Pharmacia, Uppsala, Sweden) chromatography equilibrated with Buffer A. Laccase preparations with apparent electrophoretic purity are obtained in the run-through fractions.

Example 5
Site-directed Mutagenesis of *Rhizoctonia solani* laccase Gene

Site-specific mutations are introduced into the *Rhizoctonia solani* laccase rsl4 gene of the expression plasmid, pJiWa59, using the overlap-extension PCR method (Ho, 1989, *Gene* 77: 51–59) together with the primers listed in Table 3. Primer 15 (SEQ ID NO:22) is used to create pJiWa85 that encodes three amino acid changes ("T": L466V/E467S/A468G) in the laccase coding region (Table 3). PCR amplification with primer 16 (SEQ ID NO:23) results in pJiWa86 which encodes a single amino acid mutation ("M": L470F). For each mutation, a 505 nt SacI/NorI fragment is generated by PCR and used to replace the homologous fragment in pJiWa59. PCR-amplified regions of the gene are sequenced to confirm the mutation as well as to ascertain the integrity of the coding region.

TABLE 3

Primers used for PCR mutagenesis of rsl4 gene.

| | | | | | | | | | | | | | | |
|---|---|---|---|---|---|---|---|---|---|---|---|---|---|---|
| Primer 15 | C | ATT | GAC | TGG | CAC | <u>G</u>TG | <u>TC</u>G | G<u>G</u>T | GGG | CTC | GCA | CTT | G | |
| pJiWa85 | | *I* | *D* | *W* | *H* | *V* | *S* | *G* | *G* | *L* | *A* | *L* | | (SEQ ID NO:28) |
| | | : | : | : | : | | | | : | : | : | : | | |
| RsL-wt | *H* | *I* | *D* | *W* | *H* | *L* | *E* | *A* | *G* | *L* | *A* | *L* | *V* | (SEQ ID NO:25) |
| rsl4 | CAC | ATT | GAC | TGG | CAC | TTG | GAG | GCT | GGG | CTC | GCA | CTT | GTC | (SEQ ID NO:24) |
| | | | | | | : | : | : | : | | : | : | : | |
| pJiWa86 | | | | | | *L* | *E* | *A* | *G* | *F* | *A* | *L* | *V* | (SEQ ID NO:29) |
| Primer 16 | | | | | C | TTG | GAG | GCT | GGG | <u>T</u>TC | | | GCA CTT GTC | |

Note. The amino acid translation of both the primers and the native gene are shown in italics. Homologous amino acids are noted by a colon between the two sequences. Those nucleotides in the PCR primers which differ from the gene sequence are underlined.

Example 6

Transformation of *Aspergillus oryzae* with the Modified *Rhizoctonia solani* rsl4 Genes

*Aspergillus oryzae* HowB711 is transformed with 8 $\mu$g of pJiWa85 ("T": L466V/E467S/A468G) or pJiWa86 ("M": L470F) together with 2 $\mu$g of pToC90 and *Aspergillus oryzae* HowB104 is transformed with 8 $\mu$g of pJiWa59 (wt) together with 2 $\mu$g of pToC90 using a standard PEG mediated protocol (Yelton, 1984, *Proceedings of the National Academy of Sciences USA* 81: 1470–1474). The transformants are selected on Minimal medium plates supplemented with 10 mM acetamide and 1 M sucrose. The Miruma medium is comprised of 6.0 g of $NaNO_3$, 0.52 g of KCl, 1.52 g of $KH_2PO_4$, 1.0 ml of trace metals solution, 20 g of Nobel Agar (Difco), 20 ml of 50% glucose, 20 ml of methionine (50 g/l), 20 ml of biotin (200 mg/l), 2.5 ml of 20% $MgSO_4$-$7H_2O$, and 1.0 ml of mg/ml streptomycin per liter. The agar medium is adjusted to pH 6.5 prior to autoclaving and then glucose, methionine, biotin, $MgSO_4$-$7H_2O$, and streptomycin are added as sterile solutions to the cooled autoclaved medium and poured into plates. The trace metals solution is comprised of 0.04 g of $Na_2B_4O_7$-$10H_2O$, 0.4 g of $CuSO_4$-$5H_2O$, 1.2 g of $FeSO_4$-$7H_2O$, 0.7 g of $MnSO_4$-$H_2O$, 0.8 g of $Na_2MoO_2$-$2H_2O$, and 10 g of $ZnSO_4$-$7H_2O$ per liter of RO water.

Laccase activity is scored on Minimal medium plates containing 10 mM acetamide and 1 g/l ABTS. Colonies that produce a green halo, indicative of laccase expression, are spore-purified twice.

Example 7
Expression of Modified *Rhizoctonia solani* laccases

The spores from transformants of pJiWa59 (wt), pJiWa85 ("T"), and pJiWa86 ("M") described in Example 6 are used to inoculate 15 ml of MY51 medium in 125 ml shake flasks. After 3 days and 5 days growth at 37° C., a 1 ml aliquot is removed from each shake flask and centrifuged at 14,000 g for 5 minutes to remove any mycelia clumps. The supernatants are assayed for ABTS oxidation in 96-well microtiter plates as described below.

ABTS oxidation is determined in MES pH 5.3 buffer or Britten-Robinson buffer at pH 2.7 to 11.0 in a 96-well plate at 20° C. by monitoring the absorbance change at 405 nm with an extinction coefficient of 35 mM$^{-1}$cm$^{-1}$ (Childs and Bardsley, 1975, *Biochemical Journal* 145: 93–103).

The transformants yielding the highest laccase activity are selected for fermentation and grown as described in Example 3. Laccase yields for the "M" (L470F) and "T" (L466V/E467S/A468G) mutants from these fermentations are estimated to be 17% and 50%, respectively, of the wild-type yield.

Example 8
Purification of *Rhizoctonia solani* Modified laccases

The wild-type, "M", and "T" fermentation broths from Example 7 are cheese-cloth filtered (pH 7.6, 16 mS), filtered through Whatman #2 filter paper, and concentrated on a Spiral Concentrator (Amicon) with a S1Y100 membrane (100 kDa MW-CO). The concentrated broths are then applied to a Q Sepharose column (XK26, 120 ml) (Pharmacia, Uppsala, Sweden), preequilibrated with 10 mM Tris pH 7.5, 0.7 mS (Buffer A). Active fractions run through the column during loading and washing. The active fractions are pooled, adjusted to pH 5.3 and applied on a SP-Sepharose column (XK16, 60 ml) (Pharmacia, Uppsala, Sweden), preequilibrated with 10 mM MES pH 5.3 buffer (Buffer C). The majority of activity is eluted by a linear gradient of Buffer D (Buffer C and 1 mM NaCl). The active fractions are adjusted to 20 mS and applied to a Sephadex 200 column (1610, 120 ml) (Pharmacia, Uppsala, Sweden), pre-equilibrated with Buffer E (Buffer C and 0.1 M NaCl. Purified *Rhizoctonia solani* laccase fractions are eluted by Buffer E. A recovery of 1% or 5% and purification of 280- or 150-fold are achieved for mutants "M" and "T", respectively. The "T" mutant shows a three-fold higher yield than the "M" mutant, but two-fold lower yield than the wild-type laccase.

Example 9

Characterization of the Modified *Myceliophthora thermophila* laccases and the *Rhizoctonia solani* Modified laccases The Leu/Phe mutation causes a decrease in expression yield. RsL-"M" shows a yield which is three-fold lower than that of RsL-"T", and five-fold lower than that previously obtained for RsL-wild type; while MtL-"M" shows a yield approximately two-fold lower than that observed for MtL-"T" and five-fold lower than that observed for MtL-wild type. When *Polyporus pinsitus* laccase (PpL; U.S. application Ser. No. 08/441,147, which is incorporated herein by reference), *Rhizoctonia solani* laccase (including isozyme 1 and 3; WO 95/07988), MtL, *Scytalidium thermophilum* laccase (StL), and *Myrothecium verrucaria* bilirubin oxidase (BiO) are expressed in the same host (HowB104), the yields are in the order of BiO~MtL~StL>RsL-4>RsL-1~PpL. Among these laccases, the residue corresponding to the modified Leu in the "M" mutants is: Phe for both PpL and RsL-1; Leu for RsL-4, MtL, and StL; and Met for BiO. It seems that a Phe at this particular position correlates to low expression yield of these laccases in *Aspergillus oryzae* HowB104 and HowB711 strains.

The triple mutations in RsL-mutant "T" (LEA→VSG), which eliminates the negative charge, decreases activity two orders of magnitude. The triple mutations in MtL-mutant "T" (VSG→LEA), which creates a negative charge, decreases activity 4-fold. In contrast, the "M" mutants, in which a Leu is replaced by a Phe, exhibit similar activity in comparison to their wild type counterparts. The *Rhizoctonia solani* results are consistent with the hypothesis which correlates the presence of negative charge(s) near the T1 Cu to the specific activity. The effect of the Glu in the selected pentapeptide segment could be attributed to general base-catalysis in which the negatively charged residue facilitates the electron transfer from the substrate to the T1 Cu by perturbing the substrate molecule and/or stabilizing the resulting electron-deficient intermediate or product molecule.

The molecular weights of the mature laccases are used to calculate both extinction coefficients and turnover numbers. The molecular weights are determined from the deduced amino acid sequences of the DNA sequences (FIG. 6: SEQ ID NOS:24 and 25, and FIG. 7: SEQ ID NOS:26 and 27). Protein concentrations (expressed as subunits) are measured based on the extinction coefficients determined by quantitative amino acid analysis.

Cyclic voltammetry measurements with a Pt electrode show a mid-potential of 0.76 V for $Fe(dipyridyl)_2Cl_3$—$Fe(dipyridyl)_2Cl_2$ couple in 8 mM MES pH 5.3. The oxidation of ABTS and SGZ in 8 mM MES pH 5.3 yields a mid-potential of 0.70 and 0.63 V, respectively. The published redox potentials (E°) for the redox couples $Fe(dipyridyl)_2Cl_3$—$Fe(dipyridyl)_2Cl_2$, $NaI_3$—NaI, and $K_3Fe(CN)_6$—$K_4Fe(CN)_6$ are 0.780, 0.536, and 0.433 V, respectively (Kolthoff and Tomsicek, 1936, *Journal of Physical Chemistry* 40: 247–255; O'Reilly, 1973, *Biochimica Biophysica Acta* 292: 509–515; Vanysek, 1992, In Lide, D. R., editor, *Handbook of Chemistry and Physics*, 73rd Edition, pages 8.17–8.22, CRC Press, Boca Raton, Fla.). The E° determination for *Rhizoctonia solani* laccase is performed in 8 mM MES pH 5.3 buffer with either 17 μM *Rhizoctonia solani* laccase, 0.2 mM $Fe(bipyridyl)_2Cl_2$, and 0.05–0.2 mM $Fe(bipyridyl)_2Cl_3$, or 71–78 μM *Rhizocton solani* laccase and 14–100 FμM ABTS. The E° determination for MtL is performed in 8 mM MES, pH 5.3 with 0.14 mM MtL, 0.02–20 mM $K_3Fe(CN)_6$, and 2 mM $K_4Fe(CN)_6$; as well as with 31 μM MtL, 0.1 mM $I_2$, and 5–19 mM NaI. Britten-Robinson buffer is used for other pHs. Under various potentials of the solution poised by various concentration ratios of the redox couples, the absorbance changes of laccase in the range of 550–800 nm are monitored and the concentrations of the oxidized copper (II) and reduced copper (I) states are calculated after the spectral change reaches equilibrium. The concentrations of the redox couples at equilibrium are calculated from the initial concentrations and the concentration changes caused by the interaction with laccase. In the case of measuring E° of *Rhizoctonia solani* laccase with ABTS, the concentration of ABTS cation radical (ABTS+) is measured by the absorption at 810 nm (where *Rhizoctonia solani* laccase has no contribution) and then the spectral contribution of ABTS+ at 600 nm is subtracted from the observed absorption value in order to assess the spectral change of *Rhizoctonia solani* laccase. Anaerobicity is achieved by repetitive evacuating and argon-flushing the reaction chamber at 4° C.

The mutants exhibit similar chromatographic elution patterns to their wild type counterparts. The purified preparations have a characteristic blue color typical of a laccase and show other typical laccase properties as shown in Table 4. All the mutants can be retained by a 100 kDa MW-CO membrane, indicating a dimeric nature.

TABLE 4

Properties of *Myceliophthora thermophila* and *Rhizoctonia solani* laccase mutants

| | MW*, kDa | λmax (ε)† | E° at pH 5.3‡ |
|---|---|---|---|
| pJiWa59 (wt) | 70–85 | 276 (66), 330sh (4.6), 602 (4.7) | 0.73 ± 0.02 |
| pJiWa86 ("M") | 70–90 | 276 (63), 330sh (2.6), 600 (3.7) | 0.72 ± 0.02 |
| pJiWa85 ("T") | 70–90 | 276 (63), 330sh (1.7), 600 (4.8) | 0.74 ± 0.03 |
| pRaMB17 (wt) | 75–90 | 276 (134), 330sh (8.4), 589 (4.2) | 0.47 ± 0.01 |
| pRaMB17M ("M") | 70–90 | 280 (134), 330sh (6.1), 600 (3.8) | 0.50 ± 0.01 |
| pBANe22T ("T") | 70–90 | 276 (134), 330sh (4.2), 600 (2.9) | ND¤ |

*Estimated on SDS-PAGE.
†Units: 1 max, nm; e, mM$^{-1}$cm$^{-1}$. Calculated extinction coefficients are used.
‡in V vs NHE.
¤Not determined.

$K_m$ and $k_{cat}$ are obtained from the initial rate (v), enzyme concentration (E), and substrate concentration (S) in accordance to the equation $v = k_{cat} \, ES/(K_m + S)$ by non-linear regression fitting using the Prizm program (GraphPad, San Diego, Calif.). The $K_m$ and $k_{cat}$ for ABTS and SGZ are measured spectroscopically in 8 mM MES-NaOH buffer, pH 5.3; while the values for other substrates are measured by oxygen electrode in Britten-Robinson buffer, pH 5.1 with a Hansatech DW1/AD device (Norfolk, England), with 0.4–4 µM laccase in 0.3–0.5 ml Britten-Robinson buffer. The $O_2$ concentration in air-saturated buffer solution is assumed as the same in plain water (0.28 mM).

Tables 5 and 6 summarize the SGZ and ABTS oxidase activities of the mutants. For both *Rhizoctonia solani* laccase and *Myceliophthora thermophila* laccase, more profound difference is observed on the mutant "T" than that on the mutant "M" in comparison with the wild type. FIG. 5 shows the pH-activity profiles of the mutants with ABTS and SGZ. For ABTS oxidation, a significant change is seen with RsL-"T", MtL-"M", and MtL-"Tr". The optimal pH of RsL-"T" is shifted ≧1 unit in comparison with the wild type laccase. For SGZ oxidation, an optimal pH at 7 is observed for MtL- T", in contrast to the range of 5–7 for the wild type laccase. In terms of pH profile, the elimination of the negative charge in RsL-"Tr" induces a shift of the optimal pH in the acidic direction for SGZ oxidation, probably due to the reduced acidity at the T1 site caused by the Glu removal. The creation of a negative charge in ML-"T" induces a shift of the optimal pH for activity on the allaline direction, which could be attributed to the increased acidity at MtL's T1 site caused by the creation of the negative charge.

TABLE 5

Syringaldazine oxidase activity of the mutants

| | LACU* | SOU† | (pH$_{opt}$) |
|---|---|---|---|
| RsL wt | 4.3 | 11 | (7) |
| RsL "M" | 2.2 | 4.7 | (6) |
| RsL "T" | 0.024 | 0.048 | (7) |
| MtL wt | 42 | 35 | (6) |
| MtL "M" | 24 | 25 | (6) |
| MtL "T" | 2 | 10 | (7) |

Activity unit: µmol min$^{-1}$ mg$^{-1}$.
*25 mM sodium acetate pH 5.5, 30° C.
†B & R buffer, 20° C., at optimal pH (value in parenthesis).

TABLE 6

Syringaldazine and ABTS oxidase activity of the mutants

| | SGZ | | ABTS | |
|---|---|---|---|---|
| | $K_m$, µM | $k_{cat}$, min$^{-1}$ | $K_m$, µM | $k_{cat}$, min$^{-1}$ |
| RsL wt | 28 ± 4 | 550 ± 40 | 52 ± 6 | 2500 ± 100 |
| RsL "M" | 35 ± 4 | 255 ± 11 | 125 ± 13 | 760 ± 30 |
| RsL "T" | 3.9 ± 0.3 | 1.1 ± 0.1 | 60 ± 4 | 20 ± 1 |
| MtL wt | 1.4 ± 0.2 | 4500 ± 200 | 110 ± 20 | 3800 ± 300 |
| MtL "M" | 1.8 ± 0.2 | 3300 ± 100 | 43 ± 3 | 1800 ± 100 |
| MtL: "T" | 0.9 ± 0.2 | 360 ± 20 | 11 ± 2 | 530 ± 20 |

What is claimed is:

1. A mutant of a Rhizoctonia laccase which comprises a substitution of one or more amino acid residues in one or more regions which correspond to the regions 217INVKRGKRYR226 (SEQ ID NO:25), 303LDPTNVFAVL312 (SEQ ID NO:25), 356VSLNLAIGRSTVDGIL371 (SEQ ID NO:25), 416VIELNITGGADHPI429 (SEQ ID NO:25), and 454GPWFVHCHIDWHLEAGLALVF474 (SEQ ID NO:25) of the *Rhizoctonia solani* laccase of SEQ ID NO:25 and the mutant has laccase activity.

2. The mutant of claim 1, which is a mutant of a *Rhizoctonia solani* laccase.

3. The mutant of claim 2, wherein the *Rhizoctonia solani* laccase has an amino acid sequence of SEQ ID NO:25.

4. The mutant of claim 1 which comprises a substitution of one or more amino acid residues in the region 217INVKRGKRYR226 (SEQ ID NO:25) of *Rhizoctonia solani* laccase.

5. The mutant of claim 1 which comprises a substitution of one or more amino acid residues in the region 303LDPTNVFAVL312 (SEQ ID NO:25) of *Rhizoctonia solani* laccase.

6. The mutant of claim 1 which comprises a substitution of one or more amino acid residues in the region 356VSLNLAIGRSTVDGIL371 (SEQ ID NO:25) of *Rhizoctonia solani* laccase.

7. The mutant of claim 1 which comprises a substitution of one or more amino acid residues in the region 416VIELNITGGADHPI429 (SEQ ID NO:25) of *Rhizoctonia solani* laccase.

8. The mutant of claim 1 which comprises a substitution of one or more amino acid residues in the region 454GPWFVHCHIDWHLEAGLALVF474 (SEQ ID NO:25) of *Rhizoctonia solani* laccase.

9. The mutant of claim 1 which comprises a substitution of one or more amino acid residues in the region 465HLEAGLAL472 (SEQ ID NO:25) of *Rhizoctonia solani* laccase.

10. The mutant of claim 1 which comprises a substitution of one or more amino acid residues in the region 466LEAGL470 (SEQ ID NO:25) of *Rhizoctonia solani* laccase.

11. The mutant of claim 1, wherein the mutation is a substitution of one or more amino acid residues with other amino acid residues.

12. The mutant of claim 1 in which (a) a neutral amino acid residue is substituted with a negative amino acid residue or (b) a positive amino acid residue is substituted with a negative or neutral amino acid residue.

13. The mutant of claim 1 in which a phenylalanine is substituted with another amino acid residue.

14. The mutant of claim 13 in which the other amino acid residue is a leucine.

15. The mutant of claim 1 in which (a) a neutral amino acid residue is substituted with a positive amino acid residue or (b) a negative amino acid residue is substituted with a positive or neutral amino acid residue.

16. The mutant of claim 1 in which leucine or phenylalanine is substituted with a neutral residue selected from the group consisting of histidine, serine, threonine, tyrosine, cysteine, and methionine.

17. The mutant of claim 1 which is modified by at least two amino acid residues.

18. The mutant of claim 1 which is modified by at least three amino acid residues.

19. The mutant of claim 1 which comprises the substitutions L466V/E467S/A468G.

20. The mutant of claim 1 which comprises the substitution L470F.

* * * * *

UNITED STATES PATENT AND TRADEMARK OFFICE
CERTIFICATE OF CORRECTION

PATENT NO. : 5,972,670
DATED : October 26, 1999
INVENTOR(S) : Xu Feng

It is certified that error appears in the above-identified patent and that said Letters Patent is hereby corrected as shown below:

On the title page, insert item:

[73] assignee: Novo Nordisk Biotech, Inc., 1445 Drew Avenue, Davis, Calif. 95616--

Signed and Sealed this

Thirty-first Day of October, 2000

Attest:

Q. TODD DICKINSON

*Attesting Officer*

*Director of Patents and Trademarks*